US008268796B2

(12) United States Patent
Ryan

(10) Patent No.: US 8,268,796 B2
(45) Date of Patent: Sep. 18, 2012

(54) LIPOPHILIC NUCLEIC ACID DELIVERY VEHICLE AND METHODS OF USE THEREOF

(75) Inventor: Robert O. Ryan, El Cerrito, CA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 40 days.

(21) Appl. No.: 12/997,976

(22) PCT Filed: Jun. 26, 2009

(86) PCT No.: PCT/US2009/048958
§ 371 (c)(1),
(2), (4) Date: Mar. 2, 2011

(87) PCT Pub. No.: WO2009/158678
PCT Pub. Date: Dec. 30, 2009

(65) Prior Publication Data
US 2011/0237435 A1    Sep. 29, 2011

Related U.S. Application Data

(60) Provisional application No. 61/076,521, filed on Jun. 27, 2008.

(51) Int. Cl.
*C12N 15/11* (2006.01)
(52) U.S. Cl. .................................... 514/44 A; 424/450
(58) Field of Classification Search .................. None
See application file for complete search history.

(56) References Cited

U.S. PATENT DOCUMENTS

| | | | |
|---|---|---|---|
| 4,458,066 A | 7/1984 | Caruthers et al. |
| 4,683,202 A | 7/1987 | Mullis |
| 4,970,144 A | 11/1990 | Fareed et al. |
| 5,128,318 A | 7/1992 | Levine et al. |
| 5,166,320 A | 11/1992 | Wu et al. |
| 5,490,981 A | 2/1996 | Chiknas |
| 5,514,670 A | 5/1996 | Friedman et al. |
| 5,576,016 A | 11/1996 | Amselem et al. |
| 5,733,761 A | 3/1998 | Treco et al. |
| 5,744,155 A | 4/1998 | Friedman et al. |
| 5,746,223 A | 5/1998 | Williams |
| 5,874,549 A | 2/1999 | Hadley |
| 5,877,302 A | 3/1999 | Hanson et al. |
| 5,948,441 A | 9/1999 | Lenk et al. |
| 6,288,040 B1 | 9/2001 | Müller et al. |
| 6,458,373 B1 | 10/2002 | Lambert et al. |
| 6,489,297 B1 | 12/2002 | Burman et al. |
| 6,514,523 B1 | 2/2003 | Sparks |
| 7,824,709 B2 | 11/2010 | Ryan et al. |
| 2001/0009670 A1 | 7/2001 | Williams |
| 2001/0016326 A1 | 8/2001 | Giulian |
| 2001/0016327 A1 | 8/2001 | Giulian |
| 2001/0025026 A1 | 9/2001 | Heartlein et al. |
| 2001/0028895 A1 | 10/2001 | Bisgaier et al. |
| 2001/0031262 A1 | 10/2001 | Caplan et al. |
| 2001/0031740 A1 | 10/2001 | Unger et al. |
| 2001/0038845 A1 | 11/2001 | Williams |
| 2001/0038851 A1 | 11/2001 | Allen et al. |
| 2001/0052136 A1 | 12/2001 | Lee et al. |
| 2002/0001612 A1 | 1/2002 | Papahadjopoulos et al. |
| 2002/0015941 A1 | 2/2002 | Kim et al. |
| 2002/0018806 A1 | 2/2002 | Agrawal et al. |
| 2002/0022053 A1 | 2/2002 | Williams |
| 2002/0035082 A1 | 3/2002 | Grinstaff et al. |
| 2002/0035217 A1 | 3/2002 | Uhrich |
| 2002/0041894 A1 | 4/2002 | Williams |
| 2002/0048746 A1 | 4/2002 | Lynch et al. |
| 2002/0051813 A1 | 5/2002 | Boni et al. |
| 2002/0068070 A1 | 6/2002 | Sasaki et al. |
| 2002/0071862 A1 | 6/2002 | Williams |
| 2002/0156007 A1 | 10/2002 | Graversen et al. |
| 2004/0053384 A1 | 3/2004 | Sligar et al. |
| 2010/0311595 A1 | 12/2010 | Ryan et al. |

FOREIGN PATENT DOCUMENTS

| | | |
|---|---|---|
| EP | 0 277 849 A1 | 8/1988 |
| JP | 2001-500886 A | 1/2001 |
| WO | WO-96/25942 A1 | 8/1996 |
| WO | WO-96/37608 A1 | 11/1996 |
| WO | WO-02/10501 A1 | 2/2002 |
| WO | WO-02/40501 A2 | 5/2002 |
| WO | WO-02/40501 A3 | 5/2002 |
| WO | WO-2004/050062 A2 | 6/2004 |
| WO | WO-2004/050062 A3 | 6/2004 |
| WO | WO-2004/073684 A2 | 9/2004 |
| WO | WO-2004/073684 A3 | 9/2004 |
| WO | WO-2005/039534 A1 | 5/2005 |
| WO | WO-2009/158678 A1 | 12/2009 |

OTHER PUBLICATIONS

Acsadi, G. et al. (Aug. 29, 1991). "Human Dystrophin Expression in MDX Mice After Intramuscular Injection of DNA Constructs," *Nature* 352(6338):815-818.

Anantharamaiah, G.M. et al. (Aug. 25, 1985). "Studies of Synthetic Peptide Analogs of the Amphipathic Helix," *The Journal of Biological Chemistry* 260(18):10248-10255.

Anonymous. (Feb. 1991). "Methods and Materials: Amplification of Nucleic Acid Sequences: The Choices Multiply," *The Journal of NIH Research* 3(2):81-94.

Anonymous. (1996). *Webster's Ninth New Collegiate Dictionary*, Merriam-Webster Inc.: Springfield, MA, definitions of "solicitor general" through "somatostatin," 3 pages.

Anonymous. (Apr. 30, 2004). "Sushi-Like Discs Give Inside View of Elusive Membrane Proteins," *Science* 304:674.

Anonymous. (Jul. 12, 2004). "Nanodisc: Enabling the Biochemistry of Membrane-Associated Molecules for Drug Discovery and Novel Therapeutic Applications," located at <http://www.nanodiscinc.com/technology.htm> and <http://www.nanodiscinc.com/press.shtml> visited on Jul. 12, 2004, 3 pages.

Arnhelm, N. et al. (Oct. 1, 1990). "Plymerase Chain Reaction, Transforming Genetics, Molecular Biology," *Chemical & Engineering* 68(40):36-47.

Barringer, K.J. et al. (1990). "Blunt-end and Single-strand Ligations by *Escherichia coli* Ligase: Influence on an in vitro Amplification Scheme," *Gene* 89(1):117-122.

(Continued)

*Primary Examiner* — Gollamudi Kishore
*Assistant Examiner* — Snigdha Maewall
(74) *Attorney, Agent, or Firm* — Morrison & Foerster LLP

(57) ABSTRACT

Provided herein are compositions and methods for delivery of nucleic acids to individuals and to cells, including nucleic acid delivery particles that comprising a lipid-binding polypeptide, a lipid bilayer comprising one or more cationic lipids, and a nucleic acid.

56 Claims, 4 Drawing Sheets

OTHER PUBLICATIONS

Barwicz, J. et al., (Oct. 1992). "Effects of the Aggregation State of Amphotericin B on Its Toxicity to Mice," *Antimicrobial Agents and Chemotherapy* 36(10):2310-2315.

Bayburt, T.H. et al. (1998). "Reconstitution and Imaging of a Membrane Protein in a Nanometer-Size Phospholipid Bilayer," *J. Struct. Biol.* 123:37-44.

Bayburt, T. H. et al. (2000). "Single Molecule Height Measurements on a Membrane Protein in Nanometer-Scale Phospholipid Bilayer Disks," *Langmuir* 16:5993-5997.

Bayburt, T. H. et al. (2002). "Self-Assembly of Discoidal Phospholipid Bilayer Nanoparticles With Membrane Scaffold Proteins," *Nano Letters* 2(8):853-856.

Bayburt, T. H. et al. (Nov. 2003). "Self-Assembly of Single Integral Membrane Proteins Into Soluble Nanoscale Phospholipid Bilayers," *Protein Sci.* 12:2476-2481.

Beaucage, S.L. et al. (1981). "Deoxynucleoside Phosphoramidites—A New Class of Key Intermediates for Deoxypolynucleotide Synthesis," *Tetrahedron Letters* 22(20):1859-1862.

Beckstead, J.A. et al. (2003, e-published Jul. 15, 2003). "Structure-Function Studies of Human Apolipoprotein A-V: A Regulator of Plasma Lipid Homeostasis," *Biochemistry* 42(31):9416-9423.

Beckstead, J.A. et al. (2005, e-published Feb. 19, 2005). "Combined N- and C-Terminal Truncation of Human Apolipoprotein A-I Yields a Folded, Functional Central Domain," *Biochemistry* 44(11):4591-4599.

Berger, S.L. et al. eds. (1987). *Methods in Enzymology: Guide to Molecular Cloning Techniques*, Academic Press, San Diego, CA. 152:v-x. (Table of Contents Only).

Bielicki, J.K. et al. (2002, e-published Jan. 16, 2002). "Apolipoprotein A-I$_{Milano}$ and Apolipoprotein A-I$_{Paris}$ Exhibit an Antioxidant Activity Distinct from That of Wild-Type Apolipoprotein A-I," *Biochemistry* 41(6):2089-2096.

Bittman, R. et al. (1974). "Interaction of Filipin III and Amphotericin B with Lecithin-Sterol Vesicles and Cellular Membranes. Spectral and Electron Microscope Studies," *Biochemistry* 13(7):1364-1373.

Blanche, P. J. et al. (1981). "Characterization of Human-Density Lipoproteins by Gradient Gel Electrophoresis," *Biochim Biophys. Acta*. 665(3):408-419.

Boadu, E. et al. (2008). "Cellular Cholesterol Substrate Pools for Adenosine-triphosphate Cassette Transporter A1-dependent High Density Lipoprotein Formation," *Curr. Opin. Lipidol*. 19:270-276.

Brown, E.L. et al. (1979) "Chemical Synthesis and Cloning of Tyrosine tRNA Gene," Chapter 8 in *Methods in Enzymology: Recombinant DNA*, Wu, R. ed. Academic Press, Ithaca, NY, 68:109-151.

Brown, M.S. et al. (1980). "The Scavenger Cell Pathway for Lipoprotein Degradation: Specificity of the Binding Site that Mediates the Uptake of Negatively-Charged LDL by Macrophages," *Journal of Supramolecular Structure* 13:67-81, *Membrane Transport and Neuroreceptors* 1-15.

Brushia, R.J. et al. (2001). "Baculovirus-Mediated Expression and Purification of Human Serum Paraoxonase 1A," *Journal of Lipid Research* 42:951-958.

Burke, T. G. et al. (May 25, 1993). "Lipid Bilayer Partitioning and Stability of Camptotecin Drugs," *Biochemistry* 32(20):5352-5364.

Carlson, J. W. et al., (2000, e-published Mar. 17, 2000). "Nanopatterning Phospholipid Bilayers," *Langmuir* 16(8):3927-3931.

Cheng, L. et al. (May 1993). "In vivo Promoter Activity and Transgene Expression in Mammalian Somatic Tissues Evaluated by Using Particle Bombardment," *Proc. Natl. Acad. Sci. USA* 90:4455-4459.

Clemons, K. V. et al., (Apr. 1998). "Comparison of Fungizone, Amphotec, AmBisome, and Abelcet for Treatment of Systemic Murine Cryptococcosis," *Antimicrobial Agents and Chemotherapy* 42(4):899-902.

Dass, C. R. e t al. (2000). "Apolipoprotein A-1, Phospholipid Vesicles, and Cyclodestrins as Potential Anti-Atherosclerotic Drugs: Delivery, Pharmacokinetics, and Efficacy," *Drug Delivery* 7:161-182.

Dass, C. R. e t al. (2000). "Apolipoprotein A-I, Cyclodextrins and Liposomes As Potential Drugs for the Reversal of Atherosclerosis. A Review," *J. Pharm. Pharmacol*. 52:731-761.

Denisov, I. G. et al., (2004, e-published Mar. 2, 2004). "Directed Self-Assembly of Monodisperse Phospholipid Bilayer Nanodiscs With Controlled Size," *J. Am. Chem. Soc*. 126:3477-3487.

Dettloff, M. et al. (2001, e-published Feb. 15, 2001). "An N-Terminal Three-Helix Fragment of the Exchangeable Insect Apolipoprotein Apolipophorin III Conserves the Lipid Binding Properties of Wild-Type Protein," *Biochemistry* 40(10):3150-3157.

Dettloff, M. et al. (2002, e-published Jun. 17, 2002). "Differential Lipid Binding of Truncation Mutants of *Galleria mellonella* Apolipophorin III," *Biochemistry* 41(30):9688-9695.

Dinur, T. et al. (1992). "Toward Gene Therapy for Niemann-Pick Disease (NPD): Separation of Retrovirally Corrected and Noncorrected NPD Fibroblasts Using a Novel Fluorescent Sphingomyelin," *Human Gene Therapy* 3:633-639.

Felgner, P.L. et al. (Nov. 1987). "Lipofection: A Highly Efficient, Lipid-mediated DNA-transfection Procedure," *Proc. Natl. Acad. Sci. USA* 84:7413-7417.

Fenske, D.B. et al. (2008). "Liposomal Nanomedicines," *Expert Opin.Drug Deliv* 5(1):25-44.

Ferry, N. et al. (Oct. 1991). "Retroviral-mediated Gene Transfer into Hepatocytes in vivo," *Proc. Natl. Acad. Sci. USA* 88:8377-8381.

Fire, A. et al. (Feb. 19, 1998) "Potent and Specific Genetic Interferences by Double-stranded RNA in *Caenorhabditis elegans*," *Nature* 391:806-811.

Fisher, C. A. et al. (1997). "Bacterial Overexpression, Isotope Enrichment, and NMR Analysis of the N-Terminal Domain of Human Apolipoprotein E," *Biochem. Cell Biol*. 75(1):45-53.

Fisher, C.A. et al. (1999). "Lipid Binding-Induced Conformational Changes in the N-Terminal Domain of Human Apolipoprotein E," *Journal of Lipid Research* 40:93-99.

Fisher, C.A. et al. (Oct. 27, 2000). "The Lipid-Associated Conformation of the Low Density Lipoprotein Receptor Binding Domain of Human Apolipoprotein E," *The Journal of Biological Chemistry* 275(43):33601-33606.

Forte, T.M. et al. (1999). "Targeted Disruption of the Murine Lecithin:Cholesterol Acyltransferase Gene is Associated with Reductions in Plasma Paraoxonase and Platelet-Activating Factor Acetylhydrolase Activities but not in Apolipoprotein J Concentration," *Journal of Lipid Research* 40:1276-1283.

Forte, T.M. et al. (2002). "Altered Activities of Anti-Atherogenic Enzymes LCAT, Paraoxonase, and Platelet-Activating Factor Acetylhydrolase in Atherosclerosis-Susceptible Mice," *Journal of Lipid Research* 43:477-485.

Fujii, G. et al. (1997). "The Formation of Amphotericin B Ion Channels in Lipid Bilayers," *Biochemistry* 36(16):4959-4968.

Gagoś, M. et al. (Sep.-Oct. 2005). "Binding of Antibiotic Amphotericin B to Lipid Membranes: Monomolecular Layer Technique and Linear Dichroism-FTIR Studies," *Molecular Membrane Biology* 22(5):433-442.

GenBank Accession No. NG_011793.1, last updated Feb. 27, 2011, located at <http://www.ncbi.nlm.nih.gov/nuccore/NG_011793>, last visited on Mar. 1, 2011, 17 pages.

GenBank Accession No. NM_009693.2, last updated Feb. 19, 2011, located at <http://www.ncbi.nlm.nih.gov/nuccore/NM_009693.2>, last visited on Mar. 1, 2011, 9 pages.

Goeddel, D.V. ed. (1990). *Methods in Enzymology: Gene Expression Technology*, Academic Press, San Diego, CA. 185:v-ix. (Table of Contents Only).

Goldstein, J. L. et al. (Jan. 1979). "Binding Site on Macrophages that Mediates Uptake and Degradation of Acetylated Low Density Lipoprotein, Producing Massive Cholesterol Deposition," *PNAS USA* 76(1):333-337.

Goormaghtigh, E. et al. (1999). "Attenuated Total Reflection Infrared Spectroscopy of Proteins and Lipids in Biological Membranes," *Biochimca et Biophysica Acta* 1422:105-185.

Granich, G. G. et al. (1986). "Sensitive High-Pressure Liquid Chromatographic Assay for Amphotericin B Which Incorporates an Internal Standard," *Antimicrob. Agents Chemother*. 29(4):584-588.

Guatelli, J.C. et al. (Mar. 1990). "Isothermal, In Vitro Amplification of Nucleic Acids by a Multienzyme Reaction Modeled After Retroviral Replication," *Proc. Natl. Acad. Sci. USA* 87:1874-1878.

Gurtovenko, A.A. et al. (Jun. 2004). "Cationic DMPC/DMTAP Lipid Bilayers: Molecular Dynamics Study," *Biophysical Journal* 86:3461-3472.

Hargreaves, P.L. et al. (2006). "Spectroscopic Studies of Amphotericin B Solubilized in Nanoscale Bilayer Membranes," *Biochimica et Biophysica Acta* 1758:38-44.

Herz, J. et al. (Apr. 1993). "Adenovirus-mediated Transfer of Low Density lipoprotein Receptor Gene Acutely Accelerates Cholesterol Clearance in Normal Mice," *Proc. Natl. Acad. Sci. USA* 90:2812-2816.

Innis, M.A. et al. eds. (1990). "Optimization of PCRs," Chapter 1 *in PCR Protocols A Guide to Methods and Applications*, Academic Press Inc: San Diego, CA, pp. 3-12.

Janoff, A.S. et al. (Aug. 1988). "Unusual Lipid Structures Selelctively Reduce the Toxicity of Amphotericin B," *Proc. Natl. Acad. Sci. USA* 85:6122-6126.

Jonas, A. (1986). "Reconstitution of High-Density Lipoproteins," Chapter 32 *in Methods in Enzymology: Plasma Lipoproteins, Part A: Preparation, Structure, and Molecular Biology*, Segrest, J.P. et al. eds. Academic Press, Orlando, FL, 128:553-582.

Kader, A. et al. (2002). "Loading Anticancer Drugs into HDL as Well as LDL has Little Affect on Properties of Complexes and Enhances Cytotoxicity to Human Carcinoma Cells," *Journal of Controlled Release* 80:29-44.

Kagkadis, K. A et al. (Sep.-Oct. 1996). "A Freeze-Dried Injectable Form of Ibuprofen: Development and Optimisation Using Response Surface Methodology," *PDA J. Pharm Sci. and Technol.* 50(5):317-323.

Kay, M.A. et al. (1992). "Hepatic Gene Therapy: Persistent Expression of Human $\alpha$1-Antitrypsin in Mice after Direct Gene Delivery in vivo," *Human Gene Therapy* 3:641-647.

Kiss, R.S. et al. (1993). "Physical Properties of Apolipoprotein A-I from the Chicken, *Gallus domesticus*," *Biochemistry* 32(31):7872-7878.

Kiss, R.S. et al. (1998). "Bacterial Expression and Characterization of Chicken Apolipoprotein A-I," *Protein Expresion and Purification* 12:353-360.

Kiss, R.S. et al. (1999, e-published Mar. 16, 2999). "Amphipathic $\alpha$-Helix Bundle Organization of Lipid-Free Chicken Apolipoprotein A-I," *Biochemistry* 38(14):4327-4334.

Kiss, R.S. et al. (2001). "Functional Similarities of Human and Chicken Apolipoprotein A-I: Dependence on Secondary and Tertiary Rather than Primary Structure," *Biochimica et Biophysica Acta* 1531:251-259.

Kiss, R.S. et al. (Jun. 13, 2003). "Structure-Guided Protein Engineering Modulates Helix Bundle Exchangeable Apolipoprotein Properties," *The Journal of Biological Chemistry* 278(24):21952-21959.

Kwoh, D.Y. et al. (Feb. 1989). "Transcription-Based Amplification System and Detection of Amplified Human Immunodeficiency Virus Type 1 with a Bead-Based Sandwich Hybridization Format," *Proc. Natl. Acad. Sci. USA* 86:1173-1177.

Lacko, A.G. et al. (Jul.-Aug. 2002). "High Density Lipoprotein Complexes as Delivery Vehicles for Anticancer Drugs," *Anticancer Research* 22(4):2045-2050.

Lagerstedt, J.O. et al. (Jan. 4, 2007). "EPR Spectroscopy of Site-Directed Spin Labels Reveals the Structural Heterogeneity in the N-Terminal Domain of APO-AI in Solution," *JBC Papers in Press*, located at http://www.jbc.org/cgi/doi/10.1074/jbc.M608717200, 12 pages.

Landegren, U. et al. (Aug. 26, 1988). "A Ligase-Mediated Gene Detection Technique," *Science* 241 :1077-1080.

Lister, J. (1996). "Amphotericin B Lipid Complex (Abelcet) in the Treatment of Invasive Mycoses; the American Experience," *European Journal of Haematology Supplementum* 57:18-23.

Lomell, H. et al. (1989). "Quantitative Assays Based on the Use of Replicatable Hybridization Probes," *Clinical Chemistry* 35(9):1826-1831.

Liu, H. et al. (Jan. 1993). "Prevention of Phospholipase-C Induced Aggregation of Low Density Lipoprotein by Amphipathic Apolipoproteins," *FEBS* 316(1):27-33.

Lundberg, B. B. (1998). "Biologically Active Camptothecin Derivatives for Incorporation Into Liposome Bilayers and Lipid Emulsions," *Anti-Cancer Drug Design Basingstoke* 13(5):453-461.

Madden, T.D. et al. (1990). "Incorporation of Amphotericin B Into Large Unilamellar Vesicles Composed of a Phosphatidylglycerol," *Chemistry and Physics of Lipids* 52:189-198.

Martin, D.D.O. et al. (Jul. 21, 2006). "Apolipoprotein A-I Assumes a "Looped Belt" Conformation on Reconstituted High Density Lipoprotein," *The Journal of Biological Chemistry* 281(29):20418-20426.

Memoli, A. et al. (1995). "Egg and Soya Phospholipids—Sonication and Dialysis: A Study on Liposome Characterization," *International Journal of Pharmaceutics* 117:159-163.

Narang, S.A. et al. (1979). "Improved Phosphotriester Method for the Synthesis of gene Fragments," Chapter 6 *in Methods in Enzymology: Recombinant DNA*, Wu, R. ed. Academic Press, Inc. New York, NY, 68:90-98.

Narayanaswami, V. et al. (1994). "Structural and Binding Characteristics of the Carboxyl Terminal Fragment of Apolipophorin III from *Manduca sexta*," *Biochemistry* 33(45):13312-13320.

Narayanaswami, V. et al. (1995). "Spectroscopic and Lipid Binding Studies on the Amino and Carboxyl Terminal Fragments of *Locusta migratoria* Apolipophorin III," *Biochemistry* 34(37):11822-11830.

Narayanaswami, V. et al. (Oct. 1, 1996). "Fluorescence Studies of Lipid Association-Induced Conformational Adaptations of an Exchangeable Amphipathic Apolipoprotein," *Archives of Biochemistry and Biophysics* 334(1):143-150.

Narayanaswami, V. et al. (Oct. 25, 1996). "Disulfide Bond Engineering to Monitor Conformational Opening of Apolipophorin III During Lipid Binding," *The Journal of Biological Chemistry* 271(43):26855-26862.

Narayanaswami, V. et al. (Apr. 1999). "A Molecular Trigger of Lipid Binding-Induced Opening of a Helix Bundle Exchangeable Apolipoprotein," *Proc. Natl. Acad. Sci. USA* 96:4366-4371.

Narayanaswami, V. et al. (2000). "Molecular Basis of Exchangeable Apolipoprotein Function," *Biochimica et Biophysica Acta* 1483:15-36.

Narayanaswami, V. et al. (2000). "Spectroscopic Characterization of the Conformational Adaptability of *Bombyx mori* Apolipophorin III," *Eur. J. Biochem.* 267:728-736.

Narayanaswami, V. et al. (Oct. 12, 2001). "Lipid Association-Induced N- and C-Terminal Domain Reorganization in Human Apolipoprotein E3," *The Journal of Biological Chemistry* 276(41):37853-37860.

Narayanaswami, V. et al. (Apr. 2, 2004). "Helix Orientation of the Functional Domains in Apolipoprotein E in Discoidal High Density Lipoprotein Particles," *The Journal of Biological Chemistry* 279(14):14273-14279.

Nelson, K.G. et al. (Apr. 2006). "Nanodisk-Associated Amphotericin B Clears *Leishmania major* Cutaneous Infection in Susceptible BALB/c Mice," *Antimicrobial Agents and Chemotherapy* 50(4):1238-1244.

Nguyen, T-S. et al. (Jul. 23, 2007). "Amphotericin B Induces Interdigitation of Apolipoprotein Stabilized Nanodisk Bilayers," submitted for publication to *Biochimica Biophysica Acta*, 29 pages.

Nichols, A.V. et al. (1983). "Characterization of Discoidal Complexes of Phosphatidylcholine, Apolipoprotein A-I and Cholesterol by Gradient Gel Electrophoresis," *Biochim. Biophys. Acta* 750:353-364.

Nichols, A.V. et al. (1987). "Pathways in the Formation of Human Plasma High Density Lipoprotein Subpopulations Containing Apolipoprotein A-1 Without Apolipoprotein A-II," *J. Lipid Res.* 28:719-732.

Oda, M.N. et al. (2001, e-published Jan. 19, 2001). "Cysteine Substitutions in Apolipoprotein A-I Primary Structure Modulate Paraoxonase Activity," *Biochemistry* 40(6):1710-1718.

Oda, M.N. et al. (2002). "Paraoxonase 1 Overexpression in Mice and Its Effect on High-Density Lipoproteins," *Biochemical and Biophysical Research Communications* 290(3):921-927.

Oda, M.N. et al. (Jun. 2003). "The C-Terminal Domain of Apolipoprotein A-I Contains A Lipid-Sensitive Conformational Trigger," *Nature* 10(6):455-460.

Oda, M.N. et al. (e-pub. May 19, 2003). "The C-Terminal Domain of Apolipoprotein A-I Contains a Lipid-Sensitive Conformational Trigger," *Nature Structural Biology*, pp. 1-6.

Oda, M.N. et al. (2006). "Reconstituted High-Density Lipoprotein Enriched with the Polyene Antibiotic Amphotericin B," *Journal of Lipid Research* 47:260-267.

Rajan, V. P. et al. (1988). "Differential Uptake and Metabolism of Free and Esterfied Cholesterol from High-Density Lipoproteins in the Ovary," *Biochimica et Biophysica Acta* 959:206-213.

Ramprasad, M. P. et al. (2002). "Sustained-Delivery of an ApolipoproteinE-Peptidomimeitic Using Multivesicular Liposomes Lowers Serum Cholesterol Levels," *Journal of Controlled Release* 79:207-218.

Raussens, V. et al. (May 26, 1995). "Alignment of the Apolipophorin-III α-Helices in Complex with Dimyristoylphosphatidylcholine," *The Journal of Biological Chemistry* 270(21):12542-12547.

Raussens, V. et al. (Sep. 20, 1996). "Hydrogen/Deuterium Exchange Kinetics of Apolipophorin-III in Lipid-Free and Phospholipid-Bound States," *The Journal of Biological Chemistry* 271(38):23089-23095.

Raussens, V. et al. (Oct. 2, 1998). "The Low Density Lipoprotein Receptor Active Conformation of Apolipoprotein E," *The Journal of Biological Chemistry* 273(40):25825-25830.

Raussens, V. et al. (Dec. 8, 2000). "Structural Characterization of a Low Density Lipoprotein Receptor-Active Apolipoprotein E Peptide, ApoE3-(126-183)," *The Journal of Biological Chemistry* 275(49):38329-38336.

Raussens, V. et al. (Jul. 11, 2003). "Lipid-Bound Structure of an Apolipoprotein E-Derived Peptide," *The Journal of Biological Chemistry* 278(28):25998-26006.

Redmond, K.A. et al. (2007). "All-*trans*-Retinoic Acid Nanodisks," *Int. J. Pharma.* pp. 1-5.

Rensen, P.C.N. et al. (1997). "Human Recombinant Apolipoprotein E-Enriched Liposomes Can Mimic Low-Density Lipoproteins As Carriers for the Site-Specific Delivery of Antitumor Agents," *Molecular Pharmacology* 52(3)445-455.

Rosenfeld, M.A. et al. (Jan. 10, 1992). "In vivo Transfer of the Human Cystic Fibrosis Transmembrane Conductance Regulator Gene to the Airway Epithelium," *Cell* 68:143-155.

Ruysschaert, J-M. et al. (Sep. 30, 1994). "A Novel Cationic Amphiphile for Transfection of Mammalian Cells," *Biochem. Biophys. Res. Commun.* 203(3):1622-1628.

Ryan, R.O. et al. (Jan. 25, 1993). "Conformational, Thermodynamic, and Stability Properties of *Manduca sexta* Apolipophorin III," *The Journal of Biological Chemistry* 268(3):1525-1530.

Ryan, R.O. et al. (2003). "Lipid-Protein Nanodisk Drug Delivery Vehicle," Abstract of Poster Presentation, *US and Japan Symposium on Drug Delivery*, Dec. 14-19, 2003, one page.

Ryan, R. O. (2003). "Optimized Bacterial Expression of Human Apolipoprotein A-I," *Protein Expression & Purification* 27:98-103.

Ryan, R.O. (2008). "Nanodisks: Hydrophobic drug delivery vehicles," *Expert Opin.Drug Deliv* 5(3):343-351.

Sahoo, D. et al. (Jan. 16, 1998). "Fluorescence Studies of Exchangeable Apolipoprotein-Lipid Interactions," *The Journal of Biological Chemistry* 273(3):1403-1408.

Sahoo, D. et al. (2000, e-published May 12, 2000). "Pyrene Excimer Fluorescence: A Spatially Sensitive Probe to Monitor Lipid-Induced Helical Rearrangement of Apolipophorin III," *Biochemistry* 39(22):6594-6601.

Sahoo, D. et al. (2002). "Lipid-Triggered Conformational Switch of Apolipophorin III Helix Bundle to an Extended Helix Organization." *J. Mol. Biol.* 321:201-214.

Sambrook, J. et al. (1989). *Molecular Cloning—A Laboratory Manual* Second Edition vol. 1-3, Cold Spring Harbor Laboratory Press, Cold Spring Harbor, NY, pp. v-xxxviii (Table of Contents Only).

Schouten, D. et al. (1993). "Development of Lipoprotein-Like Lipid Particles for Drug Targeting: Neo-High Density Lipoproteins," *Molecular Pharmacology* 44(2):486-492.

Segrest, J.P. et al. (1994). "The Amphipathic α Helix: A Multifunctional Structural Motif in Plasma Apolipoproteins," *Adv. Protein Chem.* 45:303-369.

Singh, T.K.A. et al. (1994). "Effect of Phospholipase C and Apolipophorin III on the Structure and Stability of Lipophorin Subspecies," *Journal of Lipid Research* 35:1561-1569.

Smith, J.D. et al. (2004). "ABCA1 Mediates Concurrent Cholesterol and Phospholipid Efflux to ApoAI," *J. Lipid Res.* 45(4), 37 pages.

Sparks, D.L. et al. (Dec. 25, 1992). "The Conformation of Apolipoprotein A-I in Discoidal and Spherical Recombinant High Density Lipoprotein Particles," *J. Biol. Chem.* 267(36):25830-25838.

Stamatatos, L. et al. (1988). "Interactions of Cationic Lipid Vesicles with Negatively Charged Phospholipid Vesicles and Biological Membranes," *Biochemistry* 27:3917-3925.

Sweetana, S. et al. (1996). "Solubility Principles and Practices for Parenteral Drug Dosage Form Development," *PDA J. Pharm Sci Tech* 50(5):330-342.

Troy, D.B. et al. eds. (2005). *Remington: The Science and Practice of Pharmacy, 21st edition*, Lippincott Williams & Wilkins, Baltimore, Maryland, pp. 1-4 (Table of Contents Only).

Tufteland, M. et al. (Jan. 19, 2007). "Peptide Stabilized Amphotericin B Nanodisks," *Peptides* 28:741-746.

Tufteland, M. et al. (2008). "Nanodisks Derived from Amphotericin B Lipid Complex," submitted for publication to *Journal of Pharmaceutical Sciences*, 24 pages.

Van Brunt, J. (Apr. 1990). "Amplifying Genes: PCR and Its Alternatives," *Biotechnology* 8:291-294.

Van Etten, E. W. M. et al., (Sep. 1998). "Superior Efficacy of Liposomal Amphotericin B With Prolonged Circulation in Blood in the Treatment of Severe Candidiasis in Leukopenic Mice," *Antimicrobial Agents and Chemotherapy* 42(9):2431-2433.

Versluis, A. J. et al. (1998). "Low-Density Lipoprotein Receptor-Mediated Delivery of A Lipophilic Daunorubicin Derivative to B16 Tumours in Mice Using Apolipoprotein E-Enriched Liposomes," *British Journal of Cancer* 78(12):1607-1614.

Versluis, A. J. et al. (1998). "Synthesis of a Lipophillic Daunorubicin Derivative and Its Incorporation Into Lipidic Carriers Developed for LDL Receptor-Mediated Tumor Therapy," *Pharmaceutical Research* 15(4):531-537.

Versluis, A. J. et al. (1999). "Stable Incorporation of a Lipophilic Daunorubicin Produg Into Apolipoprotein E-Exposing Liposomes Induces Uptake of Prodrug Via Low-Density Lipoprotein Receptor In Vivo," *The Journal of Pharmacology and Experimental Therapeutics* 289(1):1-7.

Von Dardel, O.V. (1976). "Diazepam in Emulsion Form for Intravenous Usage," *Acta Anaesth Scand.* 20:221-224.

Wang, J. et al. (Jul. 18, 1997). "Insight into Lipid Surface Recognition and Reversible Conformational Adaptations of an Exchangeable Apolipoprotein by Multidimensional Heteronuclear NMR Techniques," *The Journal of Biological Chemistry* 272(29):17912-17920.

Wang, J. et al. (1998). "Interhelical Contacts are Required for the Helix Bundle Fold of Apolipophorin III and Its Ability to Interact with Lipoproteins," *Protein Science* 7:336-341.

Wang, J. et al. (1998). "NMR Evidence for a Conformational Adaptation of Apolipophorin III Upon Lipid Association," *Biochem. Cell Biol.* 76:276-283.

Wang, J. et al. (Feb. 5, 2002). "Structural Basis for the Conformational Adaptability of Apolipophorin III, a Helix-Bundle Exchangeable Apolipoprotein," *Proc. Natl. Acad. Sci. USA* 99(3):1188-1193.

Wasan,K.M. et al. (1994). "Influence of Lipoproteins on Renal Cytotoxicity and Antifungal Activity of Amphotericin B," *Antimicrobial Agents and Chemotherapy* 38(2):223-227.

Weers, P.M.M. et al. (1994). "Factors Affecting the Stability and Conformation of *Locusta migratoria* Apolipophorin III," *Biochemistry* 33(12):3617-3624.

Weers, P.M.M. et al. (1998). "Recombinant Locust Apolipophorin III: Characterization and NMR Spectroscopy," *Biochimica et Biophysica Acta* 1393:99-107.

Weers, P.M.M. et al. (Jul. 30, 1999). "Interaction of an Exchangeable Apolipoprotein with Phospholipid Vesicles and Lipoprotein Particles," *The Journal of Biological Chemistry* 274(31):21804-21810.

Weers, P.M.M. et al. (2000). "Interaction of Locust Apolipophorin III with Lipoproteins and Phospholipid Vesicles: Effect of Glycosylation," *Journal of Lipid Research* 41:416-423.

Weers, P.M.M. et al. (2000, e-published May 18, 2000). "Lipid Binding of the Exchangeable Apolipoprotein Apolipophorin III Induces Major Changes in Fluorescence Properties of Tryptophans 115 and 130," *Biochemistry* 39(23):6874-6880.

Weers, P.M.M. et al. (2001). "Modulation of the Lipid Binding Properties of the N-Terminal Domain of Human Apolipoprotein E3," *Eur. J. Biochem.* 268:3728-3735.

Weers, P.M.M. et al. (2001, e-published May 31, 2001). "Conformational Changes of an Exchangeable Apolipoprotein, Apolipophorin III from *Locusta migratoria*, at Low pH: Correlation with Lipid Binding," *Biochemistry* 40(25):7754-7760.

Weers, P.M.M. et al. (2003). "Lipid Binding Ability of Human Apolipoprotein E N-Terminal Domain Isoforms: Correlation with Protein Stability?" *Biophysical Chemistry* 100:481-492.

Wientzek, M. et al. (Feb. 11, 1994). "Binding of Insect Apolipophorin III to Dimyristoylphosphatidylcholine Vesicles," *The Journal of Biological Chemistry* 269(6):4605-4612.

Wilson, J.M. et al. (Jan. 15, 1992). "Hepatocyte-directed Gene Transfer in vivo Leads to Transient Improvement of Hypercholesterolemia in Low Density Lipoprotein Receptor-deficient Rabbits," *The Journal of Biological Chemistry* 267(2):963-967.

Wolff, J.A. et al. (Mar. 23, 1990). "Direct Gene Transfer into Mouse Muscle in vivo," *Science* 247:1465-1468.

Wu, G.Y. et al. (Oct. 15, 1988). "Receptor-mediated Gene Delivery and Expression in vivo," *The Journal of Biological Chemistry* 263(29):14621-14624.

Wu, D.Y. et al. (1989). "The Ligation Amplification Reaction (LAR)-Amplification of Specific DNA Sequences Using Sequential Round of Template-Dependent Ligation," *Genomics* 4:560-569.

Zelenin, A.V. et al. (Jan. 1993). "Transfer of Foreign DNA into the Cells of Developing Mouse Embryos by Microprojectile Bombardment," *FEBS Letters* 315(1):29-32.

Zhang, Y. et al. (1993). "Calorimetric and Spectroscopic Studies of the Interaction of *Manduca sexta* Apolipophorin III with Zwitterionic, Anionic, and Nonionic Lipids," *Biochemistry* 32(15):3942-3952.

Zhu, N. et al. (Jul. 9, 1993). "Systemic Gene Expression after Intravenous DNA Delivery into Adult Mice," *Science* 261:209-211.

Zimmermann, T.S. et al (May 4, 2006). "RNAi-Mediated Gene Silencing in Non-Human Primates," *Nature* 441(7089):111-114. Supplemental Information: Figures 1-6 and Table 1, 7 pages, Supplemental Information: Methods, 7 pages. (18 pages total).

International Search Report mailed on Aug. 6, 2004, for PCT Patent Application No. PCT/US2004/004295, filed Feb. 13, 2004, 7 pages.

International Search Report mailed on Dec. 28, 2004, for PCT Patent Application No. PCT/US2004/025412, filed Feb. 13, 2004, 3 pages.

International Search Report mailed on Oct. 29, 2009, for PCT Patent Application No. PCT/US2009/048958, filed Jun. 26, 2009, 4 pages.

Written Opinion mailed on Oct. 29, 2009, for PCT Patent Application No. PCT/US2009/048958, filed Jun. 26, 2009, 7 pages.

LIPOPHILIC NUCLEIC ACID DELIVERY VEHICLE AND METHODS OF USE THEREOF

CROSS-REFERENCE TO RELATED APPLICATIONS

This application is a National Phase application under 35 U.S.C. §371 of International Application No. PCT/US2009/048958, filed Jun. 26, 2009, which claims benefit of U.S. Provisional Application No. 61/076,521, filed on Jun. 27, 2008, the disclosures of which are incorporated herein by reference in their entirety.

STATEMENT REGARDING FEDERALLY SPONSORED RESEARCH OR DEVELOPMENT

This invention was made with government support under grant no. HL-64159 awarded by the National Institutes of Health. The government has certain rights in the invention.

FIELD OF THE INVENTION

This application relates to compositions and methods for delivery of nucleic acids. In particular, the application relates to nucleic acid delivery particles that include a lipid-binding polypeptide, a lipid bilayer comprising one or more cationic lipids, and a nucleic acid.

BACKGROUND OF THE INVENTION

A variety of nucleic acid-based therapeutics designed to regulate aberrant gene expression associated with human disease are currently under development. Such strategies include, but are not limited to "antisense" therapy and RNA interference ("RNAi"). Antisense therapy comprises administration or in situ generation of nucleic acid molecules (i.e., RNA or DNA, or modified derivatives thereof) which specifically bind to cellular RNA (i.e., mRNA) or genomic DNA, thereby inhibiting expression of a specific protein by inhibiting its transcription and/or translation. The binding may be by conventional Watson-Crick base pairing, by specific interactions in the major groove of the double helix, or by still other types of molecular interaction (i.e., Hoogsteen base pairing). Antisense RNAs which are complementary to the 5' untranslated region of an mRNA up to and including the initiation codon work most efficiently at inhibiting translation. However, sequences complementary to the 3' untranslated sequences of mRNAs inhibit translation of mRNAs as well. Therefore, antisense RNAs complementary to either the 5' or 3' untranslated regions of a gene can be used to inhibit translation of endogenous mRNA.

RNA interference (RNAi) is an evolutionarily conserved process for specific silencing of gene expression. The discovery that synthetic short interfering RNAs (siRNAs) of ~19-29 bp can effectively inhibit gene expression in mammalian cells and animals without activating an immune response has led to a flurry of activity to develop these inhibitors as therapeutics. Inhibition is caused by the specific degradation of the messenger RNA (mRNA) transcribed from the target gene. In greater detail, RNA interference describes a process of sequence-specific post-transcriptional gene silencing in animals mediated by so called "siRNAs" (Fire et al., "Potent and specific genetic interference by double-stranded RNA in *Caenorhabditis elegans*," Nature 391:806-11 (1998)). Chemical stabilization of siRNAs results in increased serum half life, suggesting that intravenous administration may achieve positive therapeutic outcomes if delivery issues can be overcome. Consequently, synthetic short interfering RNAs (siRNAs) have emerged as an important tool for post-transcriptional gene silencing in mammalian cells and live animals.

The natural function of RNAi appears to be protection of the genome against invasion by mobile genetic elements such as retrotransposons and viruses which produce aberrant RNA or dsRNA in the host cell when they become active. The process of post-transcriptional gene silencing is therefore believed to be an evolutionarily-conserved cellular defense mechanism present in the majority of mammalian cell types and is used to prevent the expression of foreign genes such as those derived from infection of viruses. This assumption is further strengthened by the observation that RNAi in animals, and the related phenomenon of post-transcriptional gene silencing (PTGS) in plants, result from the same highly conserved mechanism, indicating an ancient origin.

RNA interference involves the processing of a double-stranded RNA (dsRNA) into shorter units (called siRNAs) that guide recognition and targeted cleavage of homologous target messenger RNA (mRNA). The first step of the process involves a dsRNA endonuclease activity (ribonuclease III-like; RNase III-like) that processes dsRNA into smaller sense and antisense RNAs in the range of 19 to 25 nucleotides long, producing the short interfering RNAs (siRNAs). That RNase III-type protein is termed "Dicer". In a second step, the siRNAs produced combine with, and serve as guides for, a different ribonuclease complex called the RNA-induced silencing complex (RISC), which recognizes and cleaves the target homologous single-stranded mRNAs.

While this technology has revolutionized research, however, inability to deliver siRNAs and other nucleic acid-based therapeutics systemically to cells remains the largest obstacle for in vivo clinical applications of such therapeutics. Although delivery of siRNA across plasma membranes can be achieved with vector-based delivery systems, high pressure intravenous injections of siRNA or chemically modified siRNAs such as cholesterol conjugated siRNAs, those technologies have intrinsic limitations.

RNA interference (RNAi) has enormous therapeutic potential. Specific gene silencing using small interfering RNA (siRNA) can disrupt virus reproduction and turn off genes related to metastatic cancer or aberrant metabolic processes, such as Alzheimer's disease. The commercial potential for this technology has yet to be realized and, in certain respects, is linked to development of viable methods for systemic delivery and targeting of siRNA.

BRIEF SUMMARY OF THE INVENTION

Provided herein are nucleic acid delivery particles comprising a lipid-binding polypeptide, a lipid bilayer, and a nucleic acid, wherein the total lipid content of the lipid bilayer is between about 5% and about 100% of one or more cationic lipids, wherein the interior of the lipid bilayer comprises a hydrophobic region, and wherein the particle does not comprise an aqueous core, is disc-shaped with the hydrophobic edge of the lipid bilayer circumscribed by the lipid-binding polypeptide at the periphery of the particle, and remains disc-shaped in aqueous solution. In certain embodiments, the nucleic acid delivery particle does not comprise a hydrophilic core. In certain embodiments, the disc shaped particle is between about 10 nm to about 40 nm in diameter. In certain embodiments, the one or more cationic lipids is selected from the group consisting of N-[1-(2,3-dioleyloxy)propyl]-N,N,N-trimethylammonium chloride (DOTMA), amidine, dimethyl-dioctadecyl ammonium bromide (DDAB), dimyristoyltrimethylammonium propane (DMTAP), and 1,2-dioleoyloxy-3-trimethylammoniopropane (DOTAP).

In certain embodiments, the total lipid content of the lipid bilayer is between about 0% to about 95% of one or more phospholipids. In certain embodiments, the one or more phospholipids is selected from the group consisting of dimyristoylphosphatidylcholine (DMPC) and dimyristoylphosphatidylglycerol (DMPG). In certain embodiments, the one or more phospholipids is selected from the group consisting of dipalmitoylphosphatidylcholine (DPPC) and egg phosphatidylcholine. In certain embodiments, the nucleic acid is a short interfering RNA (siRNA), a short hairpin RNA (shRNA), a micro RNA, an antisense RNA, an antisense DNA, an aptamer, a ribozyme, or a plasmid. In certain embodiments, the nucleic acid associates with the surface of the particle by electrostatic interactions. In certain embodiments, the nucleic acid further comprises a lipophilic conjugate, and wherein the lipophilic conjugate is incorporated into the hydrophobic region of the lipid bilayer. In certain embodiments, the lipophilic conjugate is selected from the group consisting of cholesterol, oleic acid, stearic acid, palmitic acid, myristic acid, and linoleic acid.

In certain embodiments, the lipid-binding polypeptide is an apolipoprotein. In certain embodiments, the apolipoprotein is an exchangeable apolipoprotein. In certain embodiments, the apolipoprotein is human apolipoprotein A-I. In certain embodiments, the apolipoprotein is a chimeric apolipoprotein that comprises a functional moiety. In certain embodiments, the functional moiety is a targeting moiety. In certain embodiments, the apolipoprotein has been modified to increase stability of the particle. In certain embodiments, the modification comprises introduction of cysteine residues to form intermolecular or intramolecular disulfide bonds. In certain embodiments, the apolipoprotein is modified to present uncharged amino acids in regions of the apolipoprotein adjacent to the head groups of the one or more cationic lipids. In certain embodiments, the lipid-binding polypeptide is a peptide. In certain embodiments, the lipid-binding polypeptide is an amphipathic peptide. In certain embodiments, the peptide has been modified to increase stability of the particle. In certain embodiments, the peptide is modified to present uncharged amino acids in regions of the peptide adjacent to the head groups of the one or more cationic lipids.

Provided herein are pharmaceutical compositions for the delivery of a nucleic acid comprising a nucleic acid delivery particle according to any of the above embodiments and a pharmaceutically acceptable carrier. In certain embodiments, the composition is formulated for controlled release. Also provided herein are methods for in vivo administration of a nucleic acid, comprising administering an effective amount of the pharmaceutical composition of the above embodiment to an individual. In certain embodiments, the pharmaceutical composition comprises a therapeutically effective amount of the nucleic acid. In certain embodiments, the nucleic acid is a short interfering RNA (siRNA), a short hairpin RNA (shRNA), a micro RNA, an antisense RNA, an antisense DNA, an aptamer, a ribozyme, or a plasmid. In certain embodiments, the administration is parenteral. In certain embodiments, the parenteral administration is selected from the group consisting of intravenous, intramuscular, transmucosal, and intrathecal. In certain embodiments, the composition is administered as an aerosol. In certain embodiments, the composition is formulated for controlled release.

In any of the embodiments described herein, the total lipid content of the bilayer includes about 30% of one or more cationic lipids and about 70% of one or more phospholipids. In some embodiments, the one or more phospholipids is dimyristoylphosphatidylcholine (DMPC). In some embodiments, the one or more cationic lipid is dimyristoyltrimethylammonium propane (DMTAP). In any of the embodiments described herein, the total lipid content of the bilayer includes about 30% of one or more cationic lipids and about 70% of dimyristoylphosphatidylcholine (DMPC). In any of the embodiments described herein, the total lipid content of the bilayer includes about 30% of dimyristoyltrimethylammonium propane (DMTAP) and about 70% of one or more phospholipids. In any of the embodiments described herein, the total lipid content of the bilayer includes about 30% of dimyristoyltrimethylammonium propane (DMTAP) and about 70% of dimyristoylphosphatidylcholine (DMPC).

Provided herein is a process for formulating a nucleic acid delivery particle according to claim 1, the process comprising: (1) contacting bilayer-forming lipid vesicles with a nucleic acid to form a bilayer-forming lipid vesicle-nucleic acid mixture, wherein about 5% to about 100% of the total lipid content of the vesicles is one or more cationic lipids, and (2) contacting the bilayer-forming lipid vesicle-nucleic acid mixture with a lipid-binding polypeptide. In certain embodiments, the one or more cationic lipids is selected from the group consisting of N-[1-(2,3-dioleyloxy)propyl]-N,N,N-trimethylammonium chloride (DOTMA), amidine, dimethyldioctadecyl ammonium bromide (DDAB), dimyristoyltrimethylammonium propane (DMTAP), and 1,2-dioleoyloxy-3-trimethylammoniopropane (DOTAP). In certain embodiments, the nucleic acid is a short interfering RNA (siRNA), a short hairpin RNA (shRNA), a micro RNA, an antisense RNA, an antisense DNA, an aptamer, a ribozyme, or a plasmid. In certain embodiments, the nucleic acid is solubilized in dimethylsulfoxide (DMSO) prior to contacting the bilayer-forming lipid vesicles. Also provided herein is a nucleic acid delivery particle prepared according to the above process. In certain embodiments, the nucleic acid is a short interfering RNA (siRNA), a short hairpin RNA (shRNA), a micro RNA, an antisense RNA, an antisense DNA, an aptamer, a ribozyme, or a plasmid. Also provided herein are pharmaceutical compositions comprising nucleic acid delivery particles according to the above process and a pharmaceutically acceptable carrier. In certain embodiments, the nucleic acid is a short interfering RNA (siRNA), a short hairpin RNA (shRNA), a micro RNA, an antisense RNA, an antisense DNA, an aptamer, a ribozyme, or a plasmid.

Provided herein is a process for formulating a nucleic acid delivery particle according to claim 1, said process comprising the steps of: (1) forming an aqueous dispersion of lipid vesicles, wherein said lipid vesicles comprise bilayer-forming lipids and between about 5% to about 100% of total lipid content of the vesicles is one or more cationic lipids; (2) adding a nucleic acid to the lipid vesicle dispersion to form a lipid vesicle-nucleic acid mixture; (3) adding a lipid-binding polypeptide to the lipid vesicle-nucleic acid mixture to form a lipid-nucleic acid-lipid-binding polypeptide mixture; and (4) incubating the mixture formed in step (3). In certain embodiments, the one or more cationic lipids is selected from the group consisting of N-[1-(2,3-dioleyloxy)propyl]-N,N,N-trimethylammonium chloride (DOTMA), amidine, dimethyl-dioctadecyl ammonium bromide (DDAB), dimyristoyltrimethylammonium propane (DMTAP), and 1,2-dioleoyloxy-3-trimethylammoniopropane (DOTAP). In certain embodiments, the nucleic acid is a short interfering RNA (siRNA), a short hairpin RNA (shRNA), a micro RNA, an antisense RNA, an antisense DNA, an aptamer, a ribozyme, or a plasmid. In certain embodiments, the process further comprises sonicating the mixture of step (4). In certain embodiments, the nucleic acid is solubilized in DMSO prior to addition to the lipid vesicle dispersion. Also provided herein is a nucleic acid delivery particle prepared according to the above process. In certain embodiments, the nucleic acid is a short interfering RNA (siRNA), a short hairpin RNA (shRNA), a micro RNA, an antisense RNA, an antisense DNA, an aptamer, a ribozyme, or a plasmid. Also provided are pharmaceutical compositions comprising nucleic acid delivery particles according to the above process and a pharmaceutically acceptable carrier. In certain embodiments, the nucleic acid is a short interfering RNA (siRNA), a short hairpin RNA (shRNA), a micro RNA, an antisense RNA, an antisense DNA, an aptamer, a ribozyme, or a plasmid.

In any of the embodiments described herein, the total lipid content of the lipid vesicles includes about 30% of one or more cationic lipids and about 70% of one or more phospholipids. In some embodiments, the one or more phospholipids is dimyristoylphosphatidylcholine (DMPC). In some embodiments, the one or more cationic lipid is dimyristoyltrimethylammonium propane (DMTAP). In any of the embodiments described herein, the total lipid content of the lipid vesicles includes about 30% of one or more cationic lipids and about 70% of dimyristoylphosphatidylcholine (DMPC). In any of the embodiments described herein, the total lipid content of the lipid vesicles includes about 30% of dimyristoyltrimethylammonium propane (DMTAP) and about 70% of one or more phospholipids. In any of the embodiments described herein, the total lipid content of the lipid vesicles includes about 30% of dimyristoyltrimethylammonium propane (DMTAP) and about 70% of dimyristoylphosphatidylcholine (DMPC).

Provided herein are kits comprising pharmaceutical composition according to any of the above embodiments and instructions for use in a method for administering a nucleic acid to an individual.

Provided herein are compositions for delivery of a nucleic acid to an individual, comprising a nucleic acid delivery particle and a carrier. In certain embodiments, the individual is a plant or an insect. In certain embodiments, the nucleic acid is a short interfering RNA (siRNA), a short hairpin RNA (shRNA), a micro RNA, an antisense RNA, an antisense DNA, an aptamer, a ribozyme, or a plasmid. Also provided herein are methods for delivering nucleic acids to cells comprising contacting the cell with a nucleic acid delivery particle according to any of the above embodiments.

In a further aspect is provided use of the compositions as described herein in connection with the methods as described herein, unless otherwise noted or as is clear from the specific context. The compositions as described herein may also be used in the preparation of a medicament for use in the methods as described herein.

DETAILED DESCRIPTION OF THE INVENTION

Figure 1:
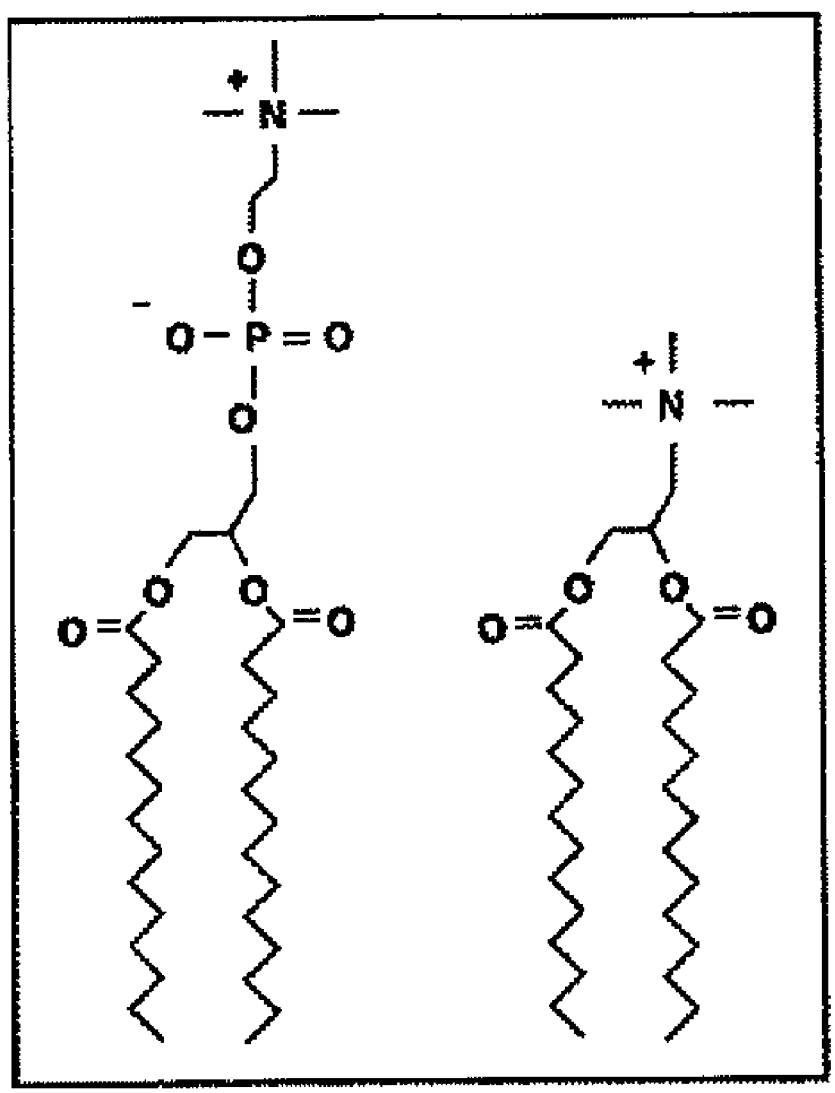
FIG. 1 shows the chemical structures of two representative bilayer-forming lipids: the zwitterionic dimyristoylphosphatidylcholine (DMPC) (left) and the cationic dimyristoyltrimethylammonium propane DMTAP (right) are shown (Gurtovenko, A. A., Patra, M., Karttunen, M. and Vattulainen, I. (2004) Cationic DMPC/DMTAP lipid bilayers: molecular dynamics study. *Biophys. J.* 86, 3461-3472).

Generally, the nucleic acid delivery particles described herein incorporate a lipid bilayer including cationic lipids, lipid binding polypeptide and nucleic acid (FIG. 1). Conferring positive charge to nanodisk particles by incorporation of cationic lipids permits the binding of nucleic acids, including, but not limited to, siRNA, microRNA, antisense RNA, antisense DNA, aptamers, ribozymes, or plasmids, via electrostatic interactions (FIG. 2) to the nanodisk particle. Formation of a stable binding interaction between nanodisk particles and nucleic acids generates a useful vehicle for transport and delivery of nucleic acids to cells and individuals. By engineering the lipid binding polypeptide component of cationic lipid nanodisks, targeting of the nucleic acid-carrying cationic lipid nanodisks (i.e., nucleic acid delivery particles) to specific cell surface receptors can be achieved. In certain embodiments, the cationic lipids are bilayer forming lipids. In certain embodiments, the cationic lipids are non-bilayer-forming lipids. In certain embodiments, the cationic lipids are a mixture of bilayer-forming and non-bilayer forming lipids.

As described herein, the nucleic acid delivery particles comprise particular combinations of components (e.g., cationic lipids, phospholipids, lipid binding polypeptides or fragments thereof, or nucleic acids) that together produce stable particles capable of binding nucleic acid molecules and delivering them to a particular target in a therapeutically effective amount while remaining disc-shaped in aqueous solution. For example, cationic lipids and phospholipids are selected that, when combined in particular ratios, form a stable lipid bilayer capable of binding nucleic acid molecules and delivering them to a particular target in a therapeutically effective amount. In addition, particular lipid binding proteins, polypeptides, or peptides (i.e., apolipoproteins or fragments thereof, chimeric or modified apolipoproteins or fragments thereof, and other lipid binding proteins or fragments thereof) are selected to minimize destabilizing interactions between the positively charged head groups of the cationic lipids and the lipid binding proteins, polypeptides, or peptides or fragments thereof, producing stable nucleic acid delivery particles that remain disc-shaped in aqueous solution, and are capable of binding nucleic acid molecules and delivering them to a particular target in a therapeutically effective amount.

Provided herein are compositions and methods for delivery of nucleic acids to an individual. In certain embodiments, the compositions comprise nucleic acid delivery particles comprising one or more lipid binding polypeptides, a lipid bilayer comprising one or more cationic lipids, and a nucleic acid. In certain embodiments, the lipid bilayer includes between about 5% to about 100% of total lipid content of one or more cationic lipids. In certain embodiments, the interior of the lipid bilayer comprises a hydrophobic region that includes hydrophobic portions of lipid molecules, e.g., the fatty acyl chains of lipids. Nanodisks are distinguished from liposomes, in which a lipid bilayer wholly encloses an aqueous or hydrophilic core. That is, in a liposome, the aqueous or hydrophilic core is surrounded by the lipid hydrophilic surfaces in a lipid bilayer. Liposomes are also spherical. In certain embodiments, the nucleic acid is associated with the surface of the particle. In certain embodiments, the particle does not comprise an aqueous core, is disc-shaped with the hydrophobic edge of the lipid bilayer circumscribed by the lipid-binding polypeptide at the periphery of the particle, is soluble in aqueous solution, and remains disc-shaped in aqueous solution. In certain embodiments, the nucleic acid delivery particle does not comprise a hydrophilic core.

In certain embodiments, the delivery particles are generally disc shaped and remain so in aqueous solution. In certain embodiments, the particles have a diameter ranging from about 10 to about 40 nm, as determined by native pore limiting gradient gel electrophoresis, in comparison with standards of known Stokes' diameter, as described, for example, in Blanche et al. (1981) *Biochim. Biophys. Acta.* 665(3): 408-19 (incorporated herein by reference in its entirety). In certain embodiments, the particles are stable (i.e., they remain disc-shaped in aqueous solution, retain the positive charge conferred by incorporation of cationic lipids, and retain the nucleic acids associated with the particle) in solution and may be lyophilized for long term storage, followed by reconstitution in aqueous solution. The lipid-binding polypeptide component defines the boundary of the discoidal bilayer and provides structure and stability to the particles.

Chimeric lipid-binding polypeptide molecules (e.g., apolipoprotein molecules) are also provided. In certain embodiments, chimeric lipid-binding polypeptide molecules are used to incorporate various additional functional properties into the nucleic acid delivery particles of the invention, including, but not limited to, targeting moieties and the like.

In certain embodiments, the nucleic acid delivery particles are administered to an individual to deliver an effective amount of a nucleic acid to the individual. In certain embodiments are provided methods for the delivery of nucleic acid to a cell, comprising contacting the cell with a nucleic acid delivery particle as described herein, in an amount effective to deliver nucleic acid to the cell. In certain embodiments, the nucleic acid is a short interfering RNA (siRNA), a short hairpin RNA (shRNA), a micro RNA (miRNA), an antisense RNA, an antisense DNA, an aptamer, a ribozyme, or a plasmid.

Nucleic Acid Delivery Particles

Provided herein are "particles" (also referred to as "delivery particles" or "nucleic acid delivery particles") that include one or more types of lipid-binding polypeptide, a lipid bilayer comprising one or more types of bilayer-forming lipid, including bilayer-forming phospholipids and/or bilayer-forming cationic lipids, and one or more nucleic acids, wherein the lipid bilayer includes at least one cationic lipid. Two representative bilayer-forming lipids are shown in FIG. 1: the zwitterionic DMPC and the cationic DMTAP. Compositions including the particles are also provided. In certain embodiments, a pharmaceutical composition is provided that includes nucleic acid delivery particles as described herein and a pharmaceutically acceptable carrier. In certain embodiments, the bilayer-forming lipids are phospholipids. In certain embodiments, the bilayer-forming lipids are cationic lipids. In certain embodiments, the bilayer-forming lipids are a mixture of phospholipids and cationic lipids. In certain embodiments, the lipid bilayer further comprises one or more types of non-bilayer-forming lipid, including non-bilayer forming phospholipids and/or non-bilayer-forming cationic lipids. In certain embodiments, the non-bilayer-forming lipids are phospholipids. In certain embodiments, the non-bilayer-forming lipids are cationic lipids. In certain embodiments, the non-bilayer-forming lipids are a mixture of phospholipids and cationic lipids.

Figure 2:
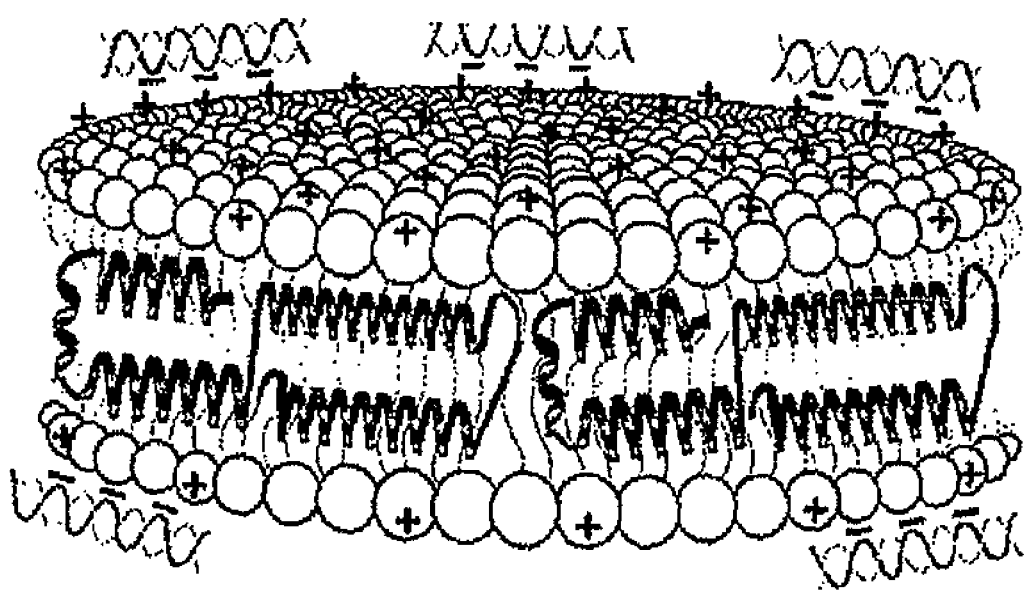
FIG. 2 is a schematic diagram of a nucleic acid delivery particle loaded with siRNA molecules showing stable binding of siRNA to the delivery particles.

In certain embodiments, the interior of a particle includes a hydrophobic region (e.g., comprised of lipid fatty acyl chains). Particles of the invention typically do not comprise a hydrophilic or aqueous core. In certain embodiments, the particles are generally disc-shaped, having a flat, discoidal, roughly circular lipid bilayer circumscribed by the lipid binding polypeptide (e.g., amphipathic α-helices and/or β-sheets of the lipid-binding polypeptides), which are associated with hydrophobic surfaces of the bilayer around the periphery of the particle. An illustrative example of a disc-shaped nucleic acid delivery particle of the invention is schematically depicted in FIG. 2.

In certain embodiments, the diameter of a disc shaped nucleic acid delivery particle is between about 10 to about 40 nm, often between about 10 to about 25 nm, often between about 15 to about 20 nm. As used herein, the term "diameter" refers to the diameter of one of the roughly circular shaped faces of the disc.

Lipid Bilayer

As used herein, the term "lipid" refers to a substance of biological or synthetic origin that is soluble or partially soluble in organic solvents or which partitions into a hydrophobic environment when present in aqueous phase. A lipid may be capable of forming a lipid bilayer (a "bilayer-forming lipid") or incapable of forming a lipid bilayer (a "non-bilayer-forming lipid"). Any bilayer-forming lipid that is capable of associating with a lipid-binding polypeptide to form a disc-shaped structure may be used in accordance with the invention. As described in greater detail herein, the lipid bilayer of the nucleic acid delivery particles will incorporate at least one cationic lipid, with, in some embodiments, the one or more cationic lipids in the lipid bilayer being between about 5% and about 100% of the total lipid content of the lipid bilayer. In certain embodiments, a nucleic acid delivery particle includes both bilayer-forming and non-bilayer-forming lipids. In certain embodiments, the lipid bilayer of a bioactive agent delivery particle includes bilayer-forming phospholipids. In certain embodiments, the lipid bilayer of a bioactive delivery particle includes non-bilayer-forming phospholipids. In certain embodiments, the lipid bilayer of a bioactive agent delivery particle includes bilayer-forming cationic lipids. In certain embodiments, the lipid bilayer of a bioactive delivery particle includes non-bilayer-forming cationic lipids.

As used herein, the term "bilayer-forming lipid" refers to a lipid that is capable of forming a lipid bilayer with a hydrophobic interior and a hydrophilic exterior. Bilayer-forming lipids include, but are not limited to, phospholipids, sphingolipids, glycolipids, alkylphospholipids, ether lipids, and plasmalogens.

The nucleic acid delivery particles provided herein include a lipid bilayer (which incorporates at least one cationic lipid as described herein), with the generally circular faces of the disc-shaped particles comprising polar head groups facing away from the interior of the particle, and the interior of the particle (i.e., the space between the circular faces) comprising a hydrophobic region of the lipid bilayer that contains hydrophobic portions of bilayer-forming lipid(s) (i.e., fatty acyl tails) and other lipid components, if present. Hydrophobic surfaces of the lipid molecules at the edge of the bilayer (the surface at the periphery of the nucleic acid delivery particle) contact the lipid-binding polypeptides of the particles, as discussed herein.

In certain embodiments, the nucleic acid delivery particles comprise one type of bilayer-forming lipid. In certain embodiments, the bilayer-forming lipid is a cationic lipid. In certain embodiments, the bilayer-forming lipid is a phospholipid. In certain embodiments, the nucleic acid delivery particles comprise a mixture of two or more types of bilayer-forming lipids. In certain embodiments, the mixture of two or more types of bilayer-forming lipids is a mixture of bilayer-forming cationic lipids and bilayer-forming phospholipids.

In certain embodiments, the nucleic acid delivery particles further comprise one type of non-bilayer-forming lipid. In certain embodiments, the non-bilayer-forming lipid is a cationic lipid. In certain embodiments, the non-bilayer-forming lipid is a phospholipid. In certain embodiments, the nucleic acid delivery particles further comprise a mixture of two or more types of non-bilayer-forming lipids. In certain embodiments, the mixture of two or more types of non-bilayer-forming lipids is a mixture of non-bilayer-forming cationic lipids and non-bilayer-forming phospholipids.

In certain embodiments, the nucleic acid delivery particles further comprise a mixture of bilayer-forming lipids and non-bilayer forming lipids. In certain embodiments, the mixture comprises bilayer-forming cationic lipids and non-bilayer forming cationic lipids. In certain embodiments, the mixture comprises bilayer-forming phospholipids and non-bilayer forming phospholipids. In certain embodiments, the mixture comprises bilayer-forming cationic lipids and non-bilayer forming phospholipids. In certain embodiments, the mixture comprises non-bilayer-forming cationic lipids and bilayer-forming phospholipids.

In certain embodiments, the nucleic acid delivery particles comprise a lipid bilayer including one or more phospholipids. Examples of suitable phospholipids include, but are not limited to, dimyristoylphosphatidylcholine (DMPC), dimyristoylphosphatidylglycerol (DMPG), 1-palmitoyl 2-oleoylphosphatidylcholine (POPC), dipalmitoylphosphatidylcholine (DPPC), dipalmitoylphosphatidylserine (DPPS), cardiolipin, dipalmitoylphosphatidylglycerol (DPPG), distearoylphosphatidylglycerol (DSPG), egg yolk phosphatidylcholine (egg PC), soy bean phosphatidylcholine (soy PC), phosphatidylinositol (PI), phosphatidic acid (PA), phosphatidylethanolamine (PE), phosphatidylserine (PS), sphingomyelin (SM), and cationic phospholipids. In certain embodiments, the nucleic acid delivery particles comprise a lipid bilayer comprising between about 0% and about 95% of one or more phospholipids. In certain embodiments, the one or more phospholipids are selected from the group consisting of dimyristoylphosphatidylcholine (DMPC) and dimyristoylphosphatidylglycerol (DMPG). In certain embodiments, the one or more phospholipids are selected from the group consisting of dipalmitoylphosphatidylcholine (DPPC) or egg phosphatidylcholine (egg PC). In certain embodiments, the one or more phospholipids are selected from the group consisting of DMPC, DMPG, DPPC, or egg PC.

The molar ratio of the one or more phospholipids comprising the lipid bilayer of the nucleic acid delivery particle can alter particle stability. In certain embodiments, the one or more phospholipids are used in a 0:100 molar ratio (the molar ratio describes the relative amounts of the different phospholipids, such that a 0:100 molar ratio refers to 0% of the first phospholipid and 100% of the second phospholipid), in a 5:95 molar ratio, in a 10:90 molar ratio, in a 15:85 molar ratio, in a 20:80 molar ratio, in a 25:75 molar ratio, in a 30:70 molar ratio, in a 35:65 molar ratio, in a 40:60 molar ratio, in a 45:55 molar ratio, in a 50:50 molar ratio, in a 55:45 molar ratio, in a 60:40 molar ratio, in a 65:35 molar ratio, in a 70:30 molar ratio, in a 75:25 molar ratio, in an 80:20 molar ratio, in an 85:15 molar ratio, in a 90:10 molar ratio, in a 95:5 molar ratio, or in a 100:0 molar ratio. In certain embodiments, the one or more phospholipids are used in a 50:50 molar ratio. In certain embodiments, the one or more phospholipids are used in a 70:30 molar ratio.

Examples of other suitable bilayer-forming lipids include cationic lipids and glycolipids. In certain embodiments, the nucleic acid delivery particles comprise a lipid bilayer including one or more cationic lipids. In certain embodiments, the nucleic acid delivery particles comprise a lipid bilayer comprising between about 5% and about 100% of one or more cationic lipids. Exemplary cationic lipids include, but are not limited to, N-[1-(2,3-dioleyloxy)propyl]-N,N,N-trimethylammonium chloride (DOTMA), amidine, dimethyl-dioctadecyl ammonium bromide (DDAB), dimyristoyltrimethylammonium propane (DMTAP), and 1,2-dioleoyloxy-3-trimethylammoniopropane (DOTAP).

The molar ratio of the one or more cationic lipids comprising the lipid bilayer of the nucleic acid delivery particle can also alter particle stability. In certain embodiments, the one or more cationic lipids are used in a 0:100 molar ratio (the molar ratio describes the relative amounts of the different phospholipids, such that a 0:100 ratio refers to 0% of the first cationic lipid and 100% of the second cationic lipid), in a 5:95 molar ratio, in a 10:90 molar ratio, in a 15:85 molar ratio, in a 20:80 molar ratio, in a 25:75 molar ratio, in a 30:70 molar ratio, in a 35:65 molar ratio, in a 40:60 molar ratio, in a 45:55 molar ratio, in a 50:50 molar ratio, in a 55:45 molar ratio, in a 60:40 molar ratio, in a 65:35 molar ratio, in a 70:30 molar ratio, in a 75:25 molar ratio, in an 80:20 molar ratio, in an 85:15 molar ratio, in a 90:10 molar ratio, in a 95:5 molar ratio, or in a 100:0 molar ratio. In certain embodiments, the one or more cationic lipids are used in a 50:50 molar ratio. In certain embodiments, the one or more cationic lipids are used in a 70:30 molar ratio.

In any of the embodiments described herein, the nucleic acid delivery particles comprise a lipid bilayer wherein the total lipid content of the bilayer includes between about 5% and about 100% of one or more cationic lipids and between about 0% to about 95% of one or more phospholipids. In any of the embodiments described herein, the total lipid content of the bilayer includes between about 10% and about 95% of one or more cationic lipids. In any of the embodiments described herein, the total lipid content of the bilayer includes between about 10% and about 90% of one or more cationic lipids. In any of the embodiments described herein, the total lipid content of the bilayer includes between about 10% and about 80% of one or more cationic lipids. In any of the embodiments described herein, the total lipid content of the bilayer includes between about 10% and about 70% of one or more cationic lipids. In any of the embodiments described herein, the total lipid content of the bilayer includes between about 10% and about 60% of one or more cationic lipids. In any of the embodiments described herein, the total lipid content of the bilayer includes between about 10% and about 50% of one or more cationic lipids. In any of the embodiments described herein, the total lipid content of the bilayer includes between about 10% and about 40% of one or more cationic lipids. In any of the embodiments described herein, the total lipid content of the bilayer includes between about 10% and about 30% of one or more cationic lipids. In any of the embodiments described herein, the total lipid content of the bilayer includes between about 10% and about 20% of one or more cationic lipids. In any of the embodiments described herein, the total lipid content of the bilayer includes between about 20% and about 80% of one or more cationic lipids. In any of the embodiments described herein, the total lipid content of the bilayer includes between about 20% and about 60% of one or more cationic lipids. In any of the embodiments described herein, the total lipid content of the bilayer includes between about 20% and about 40% of one or more cationic lipids. In any of the embodiments described herein, the total lipid content of the bilayer includes between about 30% and about 70% of one or more cationic lipids. In any of the embodiments described herein, the total lipid content of the bilayer includes between about 40% and about 60% of one or more cationic lipids. In any of the embodiments described herein, the total lipid content of the bilayer includes about 30% of one or more cationic lipids. In some embodiments, the cationic lipid is dimyristoyltrimethylammonium propane (DMTAP).

In any of the embodiments described herein, the nucleic acid delivery particles comprise a lipid bilayer wherein the total lipid content of the bilayer includes between about 5% and about 100% of one or more cationic lipids and between about 0% to about 95% of one or more phospholipids. In any of the embodiments described herein, the total lipid content of the bilayer includes about 30% of one or more cationic lipids and about 70% of one or more phospholipids. In some embodiments, the one or more phospholipids is dimyristoylphosphatidylcholine (DMPC). In some embodiments, the one or more cationic lipid is dimyristoyltrimethylammonium propane (DMTAP). In any of the embodiments described herein, the total lipid content of the bilayer includes about 30% of one or more cationic lipids and about 70% of dimyristoylphosphatidylcholine (DMPC). In any of the embodiments described herein, the total lipid content of the bilayer includes about 30% of dimyristoyltrimethylammonium propane (DMTAP) and about 70% of one or more phospholipids. In any of the embodiments described herein, the total lipid content of the bilayer includes about 30% of dimyristoyltrimethylammonium propane (DMTAP) and about 70% of dimyristoylphosphatidylcholine (DMPC). In any of the embodiments described herein, the total lipid content of the bilayer includes between about 0% and 95% of one or more phospholipids. In any of the embodiments described herein, the total lipid content of the bilayer includes between about 0% and 95% of one or more phospholipids. In any of the embodiments described herein, the total lipid content of the bilayer includes between about 5% and 90% of one or more phospholipids. In any of the embodiments described herein, the total lipid content of the bilayer includes between about 10% and 90% of one or more phospholipids. In any of the embodiments described herein, the total lipid content of the bilayer includes between about 20% and 90% of one or more phospholipids. In any of the embodiments described herein, the total lipid content of the bilayer includes between about 30% and 90% of one or more phospholipids. In any of the embodiments described herein, the total lipid content of the bilayer includes between about 40% and 90% of one or more phospholipids. In any of the embodiments described herein, the total lipid content of the bilayer includes between about 50% and 90% of one or more phospholipids. In any of the embodiments described herein, the total lipid content of the bilayer includes between about 60% and 90% of one or more phospholipids. In any of the embodiments described herein, the total lipid content of the bilayer includes between about 70% and 90% of one or more phospholipids. In any of the embodiments described herein, the total lipid content of the bilayer includes between about 80% and 90% of one or more phospholipids. In any of the embodiments described herein, the total lipid content of the bilayer includes between about 20% and 80% of one or more phospholipids. In any of the embodiments described herein, the total lipid content of the bilayer includes between about 40% and 80% of one or more phospholipids. In any of the embodiments described herein, the total lipid content of the bilayer includes between about 60% and 80% of one or more phospholipids. In any of the embodiments described herein, the total lipid content of the bilayer includes between about 30% and 70% of one or more phospholipids. In any of the embodiments described herein, the total lipid content of the bilayer includes between about 40% and 60% of one or more phospholipids. In any of the embodiments described herein, the total lipid content of the bilayer includes about 70% of one or more phospholipids.

In certain embodiments, the one or more phospholipids are used in a 0:100 molar ratio (i.e., 0% of the first phospholipid, and 100% of the second phospholipid), in a 5:95 molar ratio, in a 10:90 molar ratio, in a 15:85 molar ratio, in a 20:80 molar ratio, in a 25:75 molar ratio, in a 30:70 molar ratio, in a 35:65 molar ratio, in a 40:60 molar ratio, in a 45:55 molar ratio, in a 50:50 molar ratio, in a 55:45 molar ratio, in a 60:40 molar ratio, in a 65:35 molar ratio, in a 70:30 molar ratio, in a 75:25 molar ratio, in an 80:20 molar ratio, in an 85:15 molar ratio, in a 90:10 molar ratio, in a 95:5 molar ratio, or in a 100:0 molar ratio. In certain embodiments, the one or more phospholipids are used in a 50:50 molar ratio. In certain embodiments, the one or more phospholipids are used in a 70:30 molar ratio. In certain embodiments, the one or more phospholipids are used in molar ratios of any of at least about 1:100, 1:50, 1:20, 1:10, 1:5, 3:7, 1:2, or 1:1. In certain embodiments, the one or more cationic lipids are used in a 0:100 molar ratio (i.e., 0% of the first cationic lipid, and 100% of the second cationic lipid), in a 5:95 molar ratio, in a 10:90 molar ratio, in a 15:85 molar ratio, in a 20:80 molar ratio, in a 25:75 molar ratio, in a 30:70 molar ratio, in a 35:65 molar ratio, in a 40:60 molar ratio, in a 45:55 molar ratio, in a 50:50 molar ratio, in a 55:45 molar ratio, in a 60:40 molar ratio, in a 65:35 molar ratio, in a 70:30 molar ratio, in a 75:25 molar ratio, in an 80:20 molar ratio, in an 85:15 molar ratio, in a 90:10 molar ratio, in a 95:5 molar ratio, or in a 100:0 molar ratio. In certain embodiments, the one or more cationic lipids are used in molar ratios of any of at least about 1:100, 1:50, 1:20, 1:10, 1:5, 3:7, 1:2, or 1:1. In certain embodiments, the one or more cationic lipids are used in a 50:50 molar ratio. In certain embodiments, the one or more cationic lipids are used in a 70:30 molar ratio.

In certain embodiments, the nucleic acid delivery particles comprise a lipid bilayer including about 100% of one or more cationic lipids. In certain embodiments, the nucleic acid delivery particles comprise a lipid bilayer including about 95% of one or more cationic lipids and about 5% of one or more phospholipids. In certain embodiments, the nucleic acid delivery particles comprise a lipid bilayer including about 90% of one or more cationic lipids and about 10% of one or more phospholipids. In certain embodiments, the nucleic acid delivery particles comprise a lipid bilayer including about 80% of one or more cationic lipids and about 20% of one or more phospholipids. In certain embodiments, the nucleic acid delivery particles comprise a lipid bilayer including about 70% of one or more cationic lipids and about 30% of one or more phospholipids. In certain embodiments, the nucleic acid delivery particles comprise a lipid bilayer including about 60% of one or more cationic lipids and about 40% of one or more phospholipids. In certain embodiments, the nucleic acid delivery particles comprise a lipid bilayer including about 50% of one or more cationic lipids and about 50% of one or more phospholipids. In certain embodiments, the nucleic acid delivery particles comprise a lipid bilayer including about 40% of one or more cationic lipids and about 60% of one or more phospholipids. In certain embodiments, the nucleic acid delivery particles comprise a lipid bilayer including about 30% of one or more cationic lipids and about 70% of one or more phospholipids. In certain embodiments, the nucleic acid delivery particles comprise a lipid bilayer including about 20% of one or more cationic lipids and about 80% of one or more phospholipids. In certain embodiments, the nucleic acid delivery particles comprise a lipid bilayer including about 10% of one or more cationic lipids and about 90% of one or more phospholipids. In certain embodiments, the nucleic acid delivery particles comprise a lipid bilayer including about 5% of one or more cationic lipids and about 95% of one or more phospholipids. In certain embodiments, the nucleic acid delivery particles comprise a lipid bilayer including about 100% of one or more phospholipids.

In any of the embodiments described herein, the lipid bilayer comprises at least 25% and not more than 50% (i.e., between 25% and 49%, between 25% and 45%, between 25% and 40%, between 25% and 35%, or between 25% and 30%) of one or more cationic lipids and between at least 50% and not more than 75% of one or more phospholipids. In any of the embodiments described herein, the lipid bilayer comprises at least 30% and not more than 50% (i.e., between 30% and 49%, between 30% and 45%, between 30% and 40%, or between 30% and 35%) of one or more cationic lipids and between at least 50% and not more than 70% of one or more phospholipids. In any of the embodiments described herein, the lipid bilayer comprises at least 35% and not more than 50% (i.e., between 35% and 49%, between 35% and 45%, or between 35% and 40%) of one or more cationic lipids and between at least 50% and not more than 65% of one or more phospholipids. In certain embodiments, the one or more cationic lipids is dimyristoyltrimethylammonium propane (DMTAP).

In any of the embodiments described herein, the one or more cationic lipids are selected from the group consisting of N-[1-(2,3-dioleyloxy)propyl]-N,N,N-trimethylammonium chloride (DOTMA), amidine, dimethyl-dioctadecyl ammonium bromide (DDAB), dimyristoyltrimethylammonium propane (DMTAP), and 1,2-dioleoyloxy-3-trimethylammoniopropane (DOTAP). In any of the embodiments described herein, the one or more phospholipids are selected from the group consisting of dimyristoylphosphatidylcholine (DMPC), dimyristoylphosphatidylglycerol (DMPG), 1-palmitoyl 2-oleoylphosphatidylcholine (POPC), dipalmitoylphosphatidylcholine (DPPC), dipalmitoylphosphatidylserine (DPPS), cardiolipin, dipalmitoylphosphatidylglycerol (DPPG), distearoylphosphatidylglycerol (DSPG), egg yolk phosphatidylcholine (egg PC), soy bean phosphatidylcholine (soy PC), phosphatidylinositol (PI), phosphatidic acid (PA), phosphatidylethanolamine (PE), phosphatidylserine (PS), sphingomyelin (SM), and cationic phospholipids.

Particles may also include lipids that are not bilayer-forming lipids. Such lipids include, but are not limited to, cholesterol, cardiolipin, phosphatidylethanolamine (this lipid may form bilayers under certain circumstances), oxysterols, plant sterols, ergosterol, sitosterol, cationic lipids, cerebrosides, sphingosine, ceramide, diacylglycerol, monoacylglycerol, triacylglycerol, gangliosides, ether lipids, alkylphospholipids, plasmalogens, prostaglandins, and lysophospholipids. In some embodiments, a lipid used for preparation of a delivery particle may include one or more bound functional moieties, such as targeting moieties, nucleic acids, or tags for purification or detection.

Nucleic Acids

The delivery particles include one or more nucleic acids. In certain embodiments, a nucleic acid incorporated into a delivery particle for administration to an individual as provided herein, the nucleic acid and the delivery particle that includes the nucleic acid are substantially non-immunogenic when administered to an individual.

As used herein, the term "nucleic acid" refers to single-stranded or double-stranded DNA or RNA that is useful in research, medical treatment, diagnosis, or prophylaxis. The nucleic acid molecules provided herein include, but are not limited to short interfering RNAs (siRNA), short hairpin RNAs (shRNAs), micro RNAs, antisense RNAs, antisense DNAs, aptamers, ribozymes, or plasmids.

As used herein, the term "RNA" refers to any molecule comprising one or more ribonucleotide residues, e.g., nucleotides with a hydroxyl group at the 2' position of a D-ribofuranose moiety, including synthetically or recombinantly produced double-stranded RNA, single-stranded RNA, isolated RNA such as partially purified RNA and essentially pure RNA, as well as RNA comprising non-standard nucleotides, such as non-naturally occurring nucleotides or chemically synthesized nucleotides resistant to ribonucleases and other enzymes (for example, phosphorothioate nucleotides and the like).

As used herein, the term "essentially pure" refers to a nucleic acid preparation, for example, an RNA molecule or preparation of RNA molecules, whether natural RNA isolated from cells, or synthetically or recombinantly produced RNA prepared in a laboratory, containing an amount of contaminating compounds (e.g., DNA, protein, organic solvents, and the like) at or below the limit of detection by conventional means such as high performance liquid chromatography, ultraviolet spectroscopy, and the like. As used herein, the term "partially pure" refers to a nucleic acid preparation, for example, an RNA molecule or preparation of RNA molecules, whether natural RNA isolated from cells, or synthetically or recombinantly produced RNA prepared in a laboratory, containing a trace amount of contaminating compounds (e.g., DNA, protein, organic solvents, and the like) at or slightly above (i.e., a detectable amount but not enough to degrade the RNA preparation or otherwise affect its function) the limit of detection by conventional means such as high performance liquid chromatography, ultraviolet spectroscopy, and the like.

As used herein, the term "short interfering RNA," "small interfering RNA," or "siRNA" refers to any ribonucleic acid molecule capable of mediating RNA interference ("RNAi") or gene silencing in a sequence-specific manner. An siRNA is an RNA construct that contains one or more short sequences (typically between 19 and 29 nucleotides in length) that are at least partially complementary to and capable of interacting with a target polynucleotide sequence of interest. Interaction may be in the form of direct binding between complementary sequences of the siRNA and polynucleotide sequences of the target polynucleotide sequence, or in the form of an indirect interaction via enzymatic machinery (e.g., a protein complex) that allows the siRNA to recognize the target sequence. Recognition and binding of the target sequence by the siRNA results in cleavage of polynucleotide sequences within or near the target site recognized by the siRNA. The siRNA may comprise entirely ribonucleotide residues or may comprise one or more modified residues, particularly those modified to resist cleavage by ribonucleases.

The term "short interfering RNA" "small interfering RNA," or "siRNA" as used herein encompasses shRNA and siRNA, both of which are understood and known to those in the art to refer to RNA constructs with particular characteristics and types of configurations, including the ability to mediate RNA interference ("RNAi") or gene silencing in a sequence-specific manner. As used herein, the term "short hairpin RNA" or "shRNA" refers to an RNA sequence comprising a double-stranded region and a loop region at one end forming a hairpin loop. The double-stranded region is typically about 19 to about 29 nucleotides in length, and the loop region is typically about 2 to about 10 nucleotides in length.

As used herein, the term "micro RNA" or "miRNA" refers to short single-stranded RNA molecules, typically of about 21-23 nucleotides in length capable of regulating gene expression. miRNAs may be synthetic (i.e., recombinant) or natural. Natural miRNAs are encoded by genes that are transcribed from DNA and processed from primary transcripts ("pri-miRNA") to short stem-loop structures ("pre-miRNA"), and finally to mature miRNA. Mature miRNA molecules are partially complementary to one or more mRNA molecules, and downregulate gene expression via a process similar to RNA interference, or by inhibiting translation of mRNA.

As used herein, the term "antisense RNA" or "antisense DNA" refers to single-stranded RNA or DNA molecules of variable length that are complementary to a portion of an mRNA molecule transcribed within a cell, or to a portion of a DNA molecule. Antisense DNA may be introduced into a cell specifically to inhibit transcription of a gene by base pairing to a promoter or other regulatory sequence and physically obstructing the transcription machinery. Antisense RNA may be introduced into a cell specifically to inhibit translation of a complementary mRNA by base pairing to it and physically obstructing the translation machinery. In some cases, the dsRNA resulting from annealing of an antisense RNA to its target mRNA can trigger degradation of the transcript via processes similar to RNA interference.

As used herein, the term "aptamer" refers to nucleic acid species that have been engineered through repeated rounds of in vitro selection (also known as "selective evolution of ligands by exponential enrichment," or "SELEX") to bind to various molecular targets such as small molecules, proteins, nucleic acids, and even cells, tissues and organisms. Aptamers can be RNA or DNA, and may incorporate non-standard or modified ribonucleotides or deoxyribonucleotides.

As used herein, the term "ribozyme" or "RNA enzyme" or "catalytic RNA" refers to an RNA molecule that catalyzes a chemical reaction. Many natural ribozymes catalyze either the hydrolysis of one of their own phosphodiester bonds, or the hydrolysis of bonds in other RNAs, but they have also been found to catalyze the aminotransferase activity of the ribosome, the ligase activity of a DNA ligase, and a number of other chemical reactions performed by conventional protein enzymes.

As used herein, the term "plasmid" refers to small (i.e., less than 10 kilobase pairs), circular, single- or double-stranded DNA molecules including a selectable marker (i.e., an antibiotic resistance gene or the like) a multiple cloning site for the insertion of heterologous nucleic acid, and an origin of replication conferring the ability to replicate independently.

Chimeric Nucleic Acids

In certain embodiments, the nucleic acid further comprises a lipophilic conjugate, and the lipophilic conjugate is incorporated into the hydrophobic region of the lipid bilayer. In certain embodiments, the lipophilic conjugate is attached directly to the nucleic acid. In certain embodiments, the lipophilic conjugate is attached to the nucleic acid by means of a conventional linker or spacer molecule. As discussed above, a number of linker molecules are commercially available, for example from the Pierce Chemical Company, in Rockford, Ill. Suitable linkers include, but are not limited to, straight or branched-chain carbon linkers, heterocyclic carbon linkers, or peptide linkers. Although a linker or spacer molecule generally has no specific biological activity other than to join the molecules being combined, or to preserve some minimum distance or other spatial relationship between them, the constituent amino acids of a peptide spacer may be selected to influence some property of the molecule such as the folding, net charge, or hydrophobicity.

In certain embodiments, a chimeric nucleic acid, such as a chimeric siRNA, is prepared by chemically conjugating the nucleic acid molecule to the lipophilic group. Means of chemically conjugating molecules are well known to those of skill in the art. Such means will vary according to the structure of the moiety to be attached, but will be readily ascertainable to those of skill in the art. In certain embodiments, the nucleic acid delivery particles of the invention comprise a lipophilic conjugate selected from the group consisting of cholesterol, oleic acid, stearic acid, palmitic acid, myristic acid, and linoleic acid.

Lipid-Binding Polypeptides

As used herein, the term "lipid-binding polypeptide" refers to any synthetic or naturally occurring peptide or protein that forms a stable interaction with lipid surfaces and can function to stabilize the lipid bilayer of a particle of the invention. Particles may include one or more types of lipid-binding polypeptides, i.e., the lipid-binding polypeptides in a single particle may be identical or may be composed of two or more different polypeptide sequences. The lipid-binding polypeptides circumscribe the periphery of the particle.

In certain embodiments, lipid-binding polypeptides useful for producing the nucleic acid delivery particles provided herein include proteins having an amino acid sequence of a naturally occurring protein, or a fragment, derivative, natural variant, isoform, analog, or chimeric form thereof; proteins having a non-naturally occurring sequence; and proteins or peptides of any length that possess lipid-binding properties consistent with known apolipoproteins, and may be purified from natural sources, produced recombinantly, or produced synthetically. An analog of a naturally-occurring protein may be used. A lipid-binding polypeptide may include one or more non-natural amino acids (e.g., D-amino acids), amino acid analogs, or a peptidomimetic structure, in which the peptide bond is replaced by a structure more resistant to metabolic degradation, or individual amino acids are replaced by analogous structures. In certain embodiments, the lipid-binding polypeptide is a peptide. In certain embodiments, the peptide has been modified to increase stability of the nucleic acid delivery particle. In certain embodiments, the lipid-binding polypeptide is an amphipathic peptide. In certain embodiments, the amphipathic peptide has been modified to increase stability of the nucleic acid particle.

In certain embodiments, the lipid-binding polypeptide is an apolipoprotein. Any apolipoprotein or fragment or analog thereof may be used that is capable of associating with a lipid bilayer to form a disc-shaped particle. In certain embodiments, the nucleic acid delivery particles include exchangeable, non-exchangeable, or a mixture of exchangeable and non-exchangeable apolipoprotein molecules.

In certain embodiments of the invention, a lipid-binding polypeptide has been selected such that when the polypeptide is incorporated into a nucleic acid delivery particle as described above, the polypeptide will increase stability of the particle or confer targeting ability. In certain embodiments, the selected lipid-binding polypeptide stabilizes the particle's disc-shaped structure or conformation. In certain embodiments, the selected lipid-binding polypeptide comprises cysteine residues that permit formation of intramolecular or intermolecular disulfide bonds. In some embodiments, the lipid binding polypeptide has been selected to minimize destabilizing interactions (e.g., electrostatic interactions and the like) between those portions of the lipid-binding polypeptide proximate to the positively-charged head groups of the cationic lipids at the periphery of the particle. In some embodiments, the lipid-binding polypeptide is a peptide or a polypeptide fragment selected to minimize destabilizing interactions between those portions of the lipid-binding polypeptide proximate to the positively charged head groups of the cationic lipids at the periphery of the particle. In certain embodiments, the lipid binding polypeptide is a protein selected to minimize destabilizing interactions between those portions of the lipid binding polypeptide proximate to the positively charged head groups of the cationic lipids at the periphery of the particle. In certain embodiments, the lipid-binding polypeptide presents uncharged amino acids in regions of the polypeptide adjacent to the head groups of the one or more cationic lipids. In certain embodiments, the lipid-binding polypeptide presents negatively charged amino acids in regions of the polypeptide adjacent to the head groups of the one or more cationic lipids. In any of the embodiments described herein, the lipid-binding polypeptide may be an apolipoprotein.

Apolipoproteins generally possess a class A amphipathic α-helix structural motif (Segrest et al. (1994) *Adv. Protein Chem.* 45:303-369), and/or a β-sheet motif. Apolipoproteins generally include a high content of α-helical secondary structure with the ability to bind to hydrophobic surfaces. A characteristic feature of these proteins is their ability to interact with certain lipid bilayer vesicles and to transform them into disc-shaped complexes (for a review, see Narayanaswami and Ryan (2000) *Biochimica et Biophysica Acta* 1483:15-36). Upon contact with lipids, the protein undergoes a conformational change, adapting its structure to accommodate lipid interaction.

In certain embodiments, lipid-binding polypeptides comprising amphipathic α-helices, such as apolipoprotein molecules, are oriented circumferentially, so that the α-helices lie parallel to the surface of the nucleic acid delivery particle, like a belt surrounding the disk-shaped particle. In certain embodiments, lipid-binding polypeptides comprising amphipathic α-helices, such as apolipoprotein molecules, include one or more prolines in the α-helices that "kink" the helices, bending them such that the α-helices of the lipid-binding polypeptides are no longer in the "belt" orientation, but instead oriented perpendicularly to the surface of the nucleic acid delivery particle, like the slats of a barrel (i.e., parallel to the fatty acyl tails of the lipids comprising the lipid bilayer). See, e.g., Anantharamaiah, G. M., et al., "Studies of Synthetic Peptide Analogs of the Amphipathic Helix," *J. Biol. Chem.* 260(18):10248-255 (1985).

Generally, the predominant interaction between apolipoproteins and the lipid bilayer in a particle is through a hydrophobic interaction between residues on the hydrophobic faces of amphipathic α-helices of apolipoprotein molecules and hydrophobic surfaces of lipids, for example, phospholipid fatty acyl chains, at the edge of the bilayer at the periphery of the nucleic acid delivery particle. An amphipathic α-helix of an apolipoprotein molecule includes both a hydrophobic surface in contact with a hydrophobic surface of the lipid bilayer at the periphery of the particle, and a hydrophilic surface facing the exterior of the particle and in contact with the aqueous medium when the particle is suspended in aqueous medium. In some embodiments, an apolipoprotein may include an amphipathic β-sheet structure wherein hydrophobic residues of the β-sheet interact with lipid hydrophobic surfaces at the periphery of the disc.

A nucleic acid delivery particle often comprises about 1 to about 10 molecules of one or more types of apolipoprotein per particle. The amount of amphipathic α-helix contributed by the apolipoproteins in a particle is generally sufficient to cover the otherwise exposed hydrophobic surface of the lipid molecules located at the edge of the disc shaped lipid bilayer (i.e., the periphery of the particle). In a particular embodiment, the apolipoprotein is human apolipoprotein A-I ("ApoA-I"), the lipid bilayer includes palmitoyloleoylphosphatidylcholine, a nucleic acid delivery particle comprises 2 ApoA-1 molecules at a ratio of about 80 molecules of phospholipid to about 1 molecule of ApoA-I.

Examples of apolipoproteins which may be used for formation of the delivery particles of the invention include, but are not limited to, ApoA-I, apolipoprotein E (ApoE), and apolipophorin III (ApoIII), apolipoprotein A-IV (ApoA-IV), apolipoprotein A-V (ApoA-V), apolipoprotein C-I (ApoC-I), apolipoprotein C-II (ApoC-II), apolipoprotein C-III (ApoC-III), apolipoprotein D (ApoD), apolipoprotein A-II (ApoA-II), apolipoprotein B-48 (ApoB-48), apolipoprotein B-100 (ApoB-100), apolipoprotein J (ApoJ), apolipoprotein H (ApoH), or fragments, natural variants, isoforms, analogs, or chimeric forms thereof. In some embodiments, the apolipoprotein is human ApoA-I. In other embodiments, the apolipoprotein is the C-terminal or N-terminal domain of apolipoprotein E3, or isoforms thereof. In some embodiments, the apolipoprotein includes a functional moiety that has been attached either synthetically or recombinantly, such as a targeting moiety or a moiety having biological activity, that is not intrinsic to the apolipoprotein.

In certain embodiments, an exchangeable apolipoprotein is used. An "exchangeable apolipoprotein" may be displaced from a preformed disk-shaped nucleic acid delivery particle of the invention by another protein or peptide with lipid-binding affinity without destroying the integrity of the particle. Exchangeable apolipoproteins include synthetic or natural peptides or proteins capable of forming a stable binding interaction with lipids. More than a dozen unique exchangeable apolipoproteins have been identified in both vertebrates and invertebrates (see, e.g., Narayanaswami and Ryan, supra).

In certain embodiments, a non-exchangeable apolipoprotein is used. As used herein, the term "non-exchangeable apolipoprotein" refers to a protein or peptide that forms a stable interaction with lipid surfaces and can function to stabilize the phospholipid bilayer of particles of the invention, but cannot be removed from the surface of the particle without destroying the intrinsic structure of the particle.

Chimeric Lipid-Binding Polypeptides

As used herein, the term "chimeric" refers to two or more molecules that are capable of existing separately and are joined together to form a single molecule having the desired functionality of all of its constituent molecules. The constituent molecules of a chimeric molecule may be joined synthetically by chemical conjugation or, where the constituent molecules are all polypeptides or analogs thereof, polynucleotides encoding the polypeptides may be fused together recombinantly such that a single continuous polypeptide is expressed. Such a chimeric molecule is termed a fusion protein. As used herein, the term "fusion protein" refers to a chimeric molecule in which the constituent molecules are all polypeptides and are attached (fused) to each other such that the chimeric molecule forms a continuous single chain. The various constituents can be directly attached to each other or can be coupled through one or more linkers.

As used herein, the term "linker" or "spacer" in reference to a chimeric molecule refers to any molecule that links or joins the constituent molecules of the chimeric molecule. A number of linker molecules are commercially available, for example from the Pierce Chemical Company, in Rockford, Ill. Suitable linkers are well known to those of skill in the art and include, but are not limited to, straight or branched-chain carbon linkers, heterocyclic carbon linkers, or peptide linkers. Where the chimeric molecule is a fusion protein, the linker may be a peptide that joins the proteins comprising a fusion protein. Although a spacer generally has no specific biological activity other than to join the proteins or to preserve some minimum distance or other spatial relationship between them, the constituent amino acids of a peptide spacer may be selected to influence some property of the molecule such as the folding, net charge, or hydrophobicity.

Also provided are chimeric lipid-binding polypeptides, which may be used to prepare the nucleic acid delivery particles described above. A chimeric lipid-binding polypeptide may include one or more attached "functional moieties," such as for example, one or more targeting moieties, a moiety having a desired biological activity, an affinity tag to assist with purification, and/or a reporter molecule for characterization or localization studies. An attached moiety with biological activity may have an activity that is capable of augmenting and/or synergizing with the biological activity of a nucleic acid associated with the delivery particle. For example, a moiety with biological activity may have antimicrobial (for example, antifungal, antibacterial, anti-protozoal, bacteriostatic, fungistatic, or antiviral) activity. In certain embodiments, an attached functional moiety of a chimeric lipid-binding polypeptide is not in contact with cationic surfaces of the lipid bilayer when the lipid-binding polypeptide is incorporated into a nucleic acid delivery particle. In certain embodiments, an attached functional moiety is in contact with cationic surfaces of the lipid bilayer when the lipid-binding polypeptide is incorporated into a nucleic acid delivery particle. In certain embodiments, a functional moiety of a chimeric lipid-binding polypeptide may be intrinsic to a natural protein. In certain embodiments, a chimeric lipid-binding polypeptide includes a ligand or sequence recognized by or capable of interaction with a cell surface receptor or other cell surface moiety.

In certain embodiments, a chimeric lipid-binding polypeptide is a chimeric apolipoprotein. In certain embodiments, a chimeric apolipoprotein includes a targeting moiety that is not intrinsic to the native apolipoprotein, such as for example, S. cerevisiae α-mating factor peptide, folic acid, transferrin, lactoferrin, or a single chain variable antibody (scFv). In certain embodiments, the scFv antibody specifically binds a target antigen associated with a tissue, organ, or disease of interest such as, for example, vimentin. In certain embodiments, a chimeric apolipoprotein includes a moiety with a desired biological activity that augments and/or synergizes with the activity of a nucleic acid associated with the delivery particle, such as for example, histatin-5, magainin peptide, mellitin, defensin, colicin, N-terminal lactoferrin peptide, echinocandin, hepcidin, bactenicin, or cyclosporine. In certain embodiments, a chimeric lipid-binding polypeptide may include a functional moiety intrinsic to an apolipoprotein, for example, the intrinsic targeting moiety formed approximately by amino acids 136-150 of human ApoE, which comprises the receptor binding region recognized by members of the low density lipoprotein receptor family. Other examples of apolipoprotein intrinsic functional moieties include the region of ApoB-100 that interacts with the low density lipoprotein receptor (i.e., amino acids 3359-3367 of ApoB-100) and the region of ApoA-I that interacts with scavenger receptor type B1. In certain embodiments, a functional moiety may be added synthetically or recombinantly to produce a chimeric lipid-binding polypeptide.

In certain embodiments, a chimeric lipid-binding polypeptide, such as a chimeric apolipoprotein, is prepared by chemically conjugating the lipid-binding polypeptide molecule and the functional moiety to be attached. Means of chemically conjugating molecules are well known to those of skill in the art. Such means will vary according to the structure of the moiety to be attached, but will be readily ascertainable to those of skill in the art.

Polypeptides typically contain a variety of functional groups, e.g., carboxylic acid (—COOH), free amino (—NH$_2$), or sulfhydryl (—SH) groups, that are available for reaction with a suitable functional group on the functional moiety or on a linker to bind the moiety thereto. A functional moiety may be attached at the N-terminus, the C-terminus, or to a functional group on an interior residue (i.e., a residue at a position intermediate between the N- and C-termini) of an apolipoprotein molecule. Alternatively, the apolipoprotein and/or the moiety to be tagged can be derivatized to expose or attach additional reactive functional groups.

In certain embodiments, lipid-binding polypeptide fusion proteins that include a polypeptide functional moiety are synthesized using recombinant expression systems. Typically, this involves creating a nucleic acid (e.g., DNA) sequence that encodes the lipid-binding polypeptide and the functional moiety such that the two polypeptides will be in frame when expressed, placing the DNA under the control of a promoter, expressing the protein in a host cell, and isolating the expressed protein.

Lipid-binding polypeptide sequences and sequences encoding functional moieties as described herein may be cloned, or amplified by in vitro methods, such as, for example, the polymerase chain reaction (PCR), the ligase chain reaction (LCR), the transcription-based amplification system (TAS), or the self-sustained sequence replication system (SSR). A wide variety of cloning and in vitro amplification methodologies are well known to persons of skill. Examples of techniques sufficient to direct persons of skill through in vitro amplification methods are found for example, in Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science*, 241: 1077-1080; Van Brunt (1990) *Biotechnology*, 8: 291-294; Wu and Wallace, (1989) *Gene*, 4: 560; and Barringer et al. (1990) *Gene*, 89: 117.

In addition, DNA encoding desired fusion protein sequences may be prepared synthetically using methods that are well known to those of skill in the art, including, for example, direct chemical synthesis by methods such as the phosphotriester method of Narang et al. (1979) *Meth. Enzymol.* 68: 90-99, the phosphodiester method of Brown et al. (1979) *Meth. Enzymol.* 68: 109-151, the diethylphosphoramidite method of Beaucage et al. (1981) *Tetra. Lett.*, 22: 1859-1862, or the solid support method of U.S. Pat. No. 4,458,066.

A nucleic acid encoding a chimeric lipid-binding polypeptide fusion polypeptide can be incorporated into a recombinant expression vector in a form suitable for expression in a host cell. As used herein, the term "expression vector" refers to a nucleic acid which, when introduced into an appropriate host cell, can be transcribed and translated into a polypeptide.

The vector may also include regulatory sequences such as promoters, enhancers, or other expression control elements (e.g., polyadenylation signals). Such regulatory sequences are known to those skilled in the art (see, e.g., Goeddel (1990) *Gene Expression Technology: Meth. Enzymol.* 185, Academic Press, San Diego, Calif.; Berger and Kimmel, *Guide to Molecular Cloning Techniques, Methods in Enzymology* 152 Academic Press, Inc., San Diego, Calif.; Sambrook et al. (1989) *Molecular Cloning—A Laboratory Manual (2nd ed.) Vol.* 1-3, Cold Spring Harbor Laboratory, Cold Spring Harbor Press, NY, etc.).

In certain embodiments, a recombinant expression vector for production of a chimeric lipid-binding polypeptide is a plasmid or cosmid. In certain embodiments, the expression vector is a virus, or portion thereof, that allows for expression of a protein encoded by the nucleic acid introduced into the viral nucleic acid. For example, replication defective retroviruses, adenoviruses and adeno-associated viruses can be used. Expression vectors may be derived from bacteriophage, including all DNA and RNA phage (e.g., cosmids), or viral vectors derived from all eukaryotic viruses, such as baculoviruses and retroviruses, adenoviruses and adeno-associated viruses, Herpes viruses, Vaccinia viruses and all single-stranded, double-stranded, and partially double-stranded DNA viruses, all positive and negative stranded RNA viruses, and replication defective retroviruses. Another example of an expression vector is a yeast artificial chromosome (YAC), which contains both a centromere and two telomeres, allowing YACs to replicate as small linear chromosomes. Another example is a bacterial artificial chromosome (BAC).

The chimeric lipid-binding polypeptide fusion proteins of this invention can be expressed in a host cell. As used herein, the term "host cell" refers to any cell or cell line into which a recombinant expression vector for production of a chimeric apolipoprotein fusion protein, as described above, may be transfected for expression. Host cells include progeny of a single host cell, and the progeny may not necessarily be completely identical (in morphology or in total genomic DNA complement) to the original parent cell due to natural, accidental, or deliberate mutation. A host cell includes cells transfected or transformed in vivo with an expression vector as described above. Suitable host cells include, but are not limited to, bacterial cells (e.g., *E. coli*), fungal cells (e.g., *S. cerevisiae*), invertebrate cells (e.g., insect cells such as SF9 cells), and vertebrate cells including mammalian cells.

An expression vector encoding a chimeric lipid-binding polypeptide fusion protein can be transfected into a host cell using standard techniques. As used herein, the terms "transfection" or "transformation" refer to the insertion of an exogenous polynucleotide into a host cell. The exogenous polynucleotide may be maintained as a non-integrated vector, such as for example a plasmid, or alternatively may be integrated into the host cell genome. Examples of transfection techniques include, but are not limited to, calcium phosphate co-precipitation, DEAE-dextran-mediated transfection, lipofection, electroporation and microinjection. Suitable methods for transfecting host cells can be found in Sambrook et al. (1989) *Molecular Cloning: A Laboratory Manual,* 2nd ed., Cold Spring Harbor Laboratory Press, and other laboratory textbooks. Nucleic acid can also be transferred into cells via a delivery mechanism suitable for introduction of nucleic acid into cells in vivo, such as via a retroviral vector (see e.g., Ferry et al. (1991) *Proc. Natl. Acad. Sci., USA,* 88: 8377-8381; and Kay et al. (1992) *Human Gene Therapy* 3: 641-647), an adenoviral vector (see, e.g., Rosenfeld (1992) *Cell* 68: 143-155; and Herz and Gerard (1993) *Proc. Natl. Acad. Sci., USA,* 90:2812-2816), receptor-mediated DNA uptake (see e.g., Wu, and Wu (1988) *J. Biol. Chem.* 263: 14621; Wilson et al. (1992) *J. Biol. Chem.* 267: 963-967; and U.S. Pat. No. 5,166, 320), direct injection of DNA (see, e.g., Acsadi et al. (1991) *Nature* 332: 815-818; and Wolff et al. (1990) *Science* 247: 1465-1468) or particle bombardment (biolistics) (see e.g., Cheng et al. (1993) *Proc. Natl. Acad. Sci., USA,* 90:4455-4459; and Zelenin et al. (1993) *FEBS Letts.* 315: 29-32).

Once expressed, the chimeric lipid-binding polypeptides may be purified according to standard procedures of the art, including, but not limited to affinity purification, ammonium sulfate precipitation, ion exchange chromatography, or gel electrophoresis.

In certain embodiments, a chimeric lipid-binding polypeptide may be produced using a cell free expression system or via solid-state peptide synthesis.

Modified Lipid-Binding Polypeptides

In certain embodiments of the invention, a lipid-binding polypeptide is provided that has been modified such that when the polypeptide is incorporated into a nucleic acid delivery particle as described above, the modification will increase stability of the particle or confer targeting ability. In certain embodiments, the modification permits the lipid-binding polypeptides of a particle to stabilize the particle's disc-shaped structure or conformation. In certain embodiments, the modification includes introduction of cysteine residues into apolipoprotein molecules to permit formation of intramolecular or intermolecular disulfide bonds, e.g., by site-directed mutagenesis. In certain embodiments, a chemical crosslinking agent is used to form intermolecular links between apolipoprotein molecules to enhance stability of the particles. Intermolecular crosslinking prevents or reduces dissociation of apolipoprotein molecules from the particles and/or prevents displacement by apolipoprotein molecules within an individual to whom the particles are administered. In some embodiments, the lipid binding polypeptide has been modified to reduce destabilizing interactions (e.g., electrostatic interactions and the like) between those portions of the lipid-binding polypeptide proximate to the positively-charged head groups of the cationic lipids at the periphery of the particle. In some embodiments, the lipid-binding polypeptide is a peptide designed to reduce destabilizing interactions between those portions of the lipid-binding polypeptide proximate to the positively charged head groups of the cationic lipids at the periphery of the particle. In certain embodiments, the lipid binding polypeptide is a protein modified (e.g., with insertion(s), deletion(s) or chemical modification(s) of particular amino acid residues) to reduce destabilizing interactions between those portions of the lipid binding polypeptide proximate to the positively charged head groups of the cationic lipids at the periphery of the particle. In certain embodiments, the lipid-binding polypeptide is modified to present uncharged amino acids in regions of the polypeptide adjacent to the head groups of the one or more cationic lipids. In certain embodiments, the lipid-binding polypeptide is modified to present negatively charged amino acids in regions of the polypeptide adjacent to the head groups of the one or more cationic lipids. In any of the embodiments described herein, the lipid-binding polypeptide may be an apolipoprotein.

In certain embodiments, a lipid-binding polypeptide is modified either by chemical derivatization of one or more amino acid residues or by site-directed mutagenesis to confer targeting ability to or recognition by a cell surface receptor. In certain embodiments, the lipid binding polypeptide is modified to confer the ability to target cellular receptors involved in the uptake of various lipoproteins or lipoprotein particles, such as very low density lipoproteins (VLDL), intermediate density lipoproteins (IDL), low density lipoproteins (LDL), high density lipoproteins (HDL), or chylomicrons.

Delivery System for Delivery of a Nucleic Acid to an Individual

Also provided is a delivery system for delivering nucleic acids to an individual, comprising nucleic acid delivery particles as described above and a carrier, optionally a pharmaceutically acceptable carrier. In certain embodiments, the delivery system comprises an effective amount of the nucleic acid.

As used herein, the term "individual" refers to any prokaryote or eukaryote to which one desires to deliver nucleic acids. In certain embodiments, the individual is a prokaryote such as a bacterium. In certain embodiments, the individual is a eukaryote, such as a fungus, a plant, an invertebrate animal, such as an insect, or a vertebrate animal. In certain embodiments, the individual is a vertebrate, such as a human, a nonhuman primate, an experimental animal, such as a mouse or rat, a pet animal, such as a cat or dog, or a farm animal, such as a horse, sheep, cow, or pig, a bird (i.e., avian individual), or a reptile (i.e., reptilian individual).

In certain embodiments, nucleic acid delivery particles are formulated in a suitable carrier for administration to an individual. As used herein, the term "carrier" refers to a relatively inert substance that facilitates administration of nucleic acid. For example, a carrier can give form or consistency to the composition or can act as a diluent. As used herein, the term "pharmaceutically acceptable carriers" refer to carriers that are biocompatible (i.e., not toxic to the host) and suitable for a particular route of administration for a pharmacologically effective substance. Suitable pharmaceutically acceptable carriers include but are not limited to stabilizing agents, wetting and emulsifying agents, salts for varying osmolarity, encapsulating agents, buffers, and skin penetration enhancers. Examples of pharmaceutically acceptable carriers are described in *Remington: The Science and Practice of Pharmacy* (Philip R. Gerbino, ed., 21st edition, 2005). In some embodiments, the pharmaceutical compositions described herein are suitable for in vivo or ex vivo administration to an individual, wherein the individual is a vertebrate.

As used herein, the term "effective amount" refers to an amount of nucleic acid sufficient to affect a desired result such as, for example, a decrease in expression (i.e., transcription or translation) of a gene. A "therapeutically effective amount" or "therapeutic dose" refers to an amount of nucleic acid sufficient to affect beneficial clinical results such as, for example, reduction or alleviation of a symptom of a disease, reduction or alleviation of a fungal or bacterial infection, and the like.

In certain embodiments, the nucleic acid delivery system is a pharmaceutical composition comprising a nucleic acid delivery particle and a pharmaceutically acceptable carrier. In certain embodiments, the pharmaceutical composition comprises nucleic acid associated with a lipid bilayer (i.e., a nucleic acid delivery particle) and a pharmaceutically acceptable carrier. In certain embodiments, the nucleic acid delivery particle and the nucleic acid are non-immunogenic when administered to an individual. Immunogenicity may be measured by methods that are well known in the art. For example, immunogenicity may be assessed by an ELISA method, i.e., by probing serum from an individual to whom nucleic acid delivery particles have been administered for antibody binding to an equivalent amount of nucleic acid delivery particles bound to an immunosorbent plate. In any of the embodiments described herein, the pharmaceutical composition is formulated for controlled or extended release.

Methods of Use

In a further aspect, methods are provided for administration of a nucleic acid to an individual (as described herein), comprising administering an effective amount of any one or more of the compositions described herein to an individual. In some embodiments are provided are methods for in vivo administration of a nucleic acid, comprising administering an effective amount of any one or more of the pharmaceutical compositions described herein to an individual. In certain embodiments, the individual is a vertebrate. In certain embodiments, the pharmaceutical composition comprises a nucleic acid delivery particle as described above, the particle including a lipid-binding polypeptide, a lipid bilayer comprising at least about 5% to at most about 100% of one or more cationic lipids and at least about 0% to at most about 95% of one or more phospholipids, and a nucleic acid, wherein the interior of the particle includes hydrophobic surfaces of the lipid bilayer (i.e., fatty acyl chains).

In certain embodiments, the lipid bilayer comprises at least about 10% and at most about 90% of one or more cationic lipids and at least about 10% and at most about 90% of one or more phospholipids. In certain embodiments, the lipid bilayer comprises at least about 20% and at most about 80% of one or more cationic lipids and at least about 20% and at most about 80% of one or more phospholipids. In certain embodiments, the lipid bilayer comprises at least about 30% and at most about 70% of one or more cationic lipids and at least about 30% and at most about 70% of one or more phospholipids. In certain embodiments, the lipid bilayer comprises at least about 40% and at most about 60% of one or more cationic lipids and at least about 40% and at most about 60% of one or more phospholipids. In certain embodiments, the lipid bilayer comprises about 50% of one or more cationic lipids and about 50% of one or more phospholipids.

In any of the embodiments described herein, the lipid bilayer comprises at least 25% and not more than 50% (i.e., between 25% and 49%, between 25% and 45%, between 25% and 40%, between 25% and 35%, or between 25% and 30%) of one or more cationic lipids and between at least 50% and not more than 75% of one or more phospholipids. In any of the embodiments described herein, the lipid bilayer comprises at least 30% and not more than 50% (i.e., between 30% and 49%, between 30% and 45%, between 30% and 40%, or between 30% and 35%) of one or more cationic lipids and between at least 50% and not more than 70% of one or more phospholipids. In any of the embodiments described herein, the lipid bilayer comprises at least 35% and not more than 50% (i.e., between 35% and 49%, between 35% and 45%, or between 35% and 40%) of one or more cationic lipids and between at least 50% and not more than 65% of one or more phospholipids. In certain embodiments, the one or more cationic lipids is dimyristoyltrimethylammonium propane (DMTAP).

In certain embodiments, the lipid bilayer comprises about 30% of one or more cationic lipids and about 70% of one or more phospholipids. In certain embodiments, the one or more phospholipids is dimyristoylphosphatidylcholine (DMPC). In certain embodiments, the one or more cationic lipid is dimyristoyltrimethylammonium propane (DMTAP). In certain embodiments, the lipid bilayer comprises about 30% of one or more cationic lipids and about 70% of dimyristoylphosphatidylcholine (DMPC). In certain embodiments, the lipid bilayer comprises about 30% of dimyristoyltrimethylammonium propane (DMTAP) and about 70% of one or more phospholipids. In certain embodiments, the lipid bilayer comprises about 30% of dimyristoyltrimethylammonium propane (DMTAP) and about 70% of dimyristoylphosphatidylcholine (DMPC).

In certain embodiments, the pharmaceutical composition comprises a therapeutically effective amount of the nucleic acid. In certain embodiments, the nucleic acid being administered is a short interfering RNA (siRNA), a short hairpin RNA (shRNA), a micro RNA (miRNA), an antisense RNA, an antisense DNA, an aptamer, a ribozyme, or a plasmid. In certain embodiments, a therapeutically effective amount of the nucleic acid delivery particles is administered, optionally in a pharmaceutically acceptable carrier. Generally, the particles are disc shaped, with a diameter between about 10 nm to about 40 nm, as measured by native pore limiting gradient gel electrophoresis.

The route of administration may vary according to the individual, or the condition to be treated. Where the individual is a mammal, generally administration is parenteral. Routes of administration include, but are not limited to, intravenous, intramuscular, subcutaneous, transmucosal, nasal, intrathecal, topical, intraperitoneal, and transdermal. In certain embodiments, the pharmaceutical composition comprises a solution of nucleic acid delivery particles for parenteral administration. In certain embodiments, the pharmaceutical composition comprising nucleic acid delivery particles is administered as an aerosol. In certain embodiments, the pharmaceutical composition comprising nucleic acid delivery particles is administered nasally. In certain embodiments, the pharmaceutical composition comprising nucleic acid delivery particles is administered via inhalation. In certain embodiments, the pharmaceutical composition is formulated for controlled or extended release. Nucleic acid delivery particles may be formulated in a pharmaceutically acceptable form for administration to an individual, optionally in a pharmaceutically acceptable carrier or excipient. In certain embodiments, the nucleic acid delivery particles are formulated for controlled or extended release.

For preparing such compositions, methods well known in the art may be used, and any pharmaceutically acceptable carriers, diluents, excipients, or other additives normally used in the art can be used.

The nucleic acid delivery particles of the present invention can be made into pharmaceutical compositions by combination with appropriate medical carriers or diluents. For example, the delivery particles can be solubilized in solvents commonly used in the preparation of injectable solutions, such as for example, physiological saline, water, or aqueous dextrose. Other suitable pharmaceutical carriers and their formulations are described in *Remington: The Science and Practice of Pharmacy*, supra. Such formulations may be made up in sterile vials containing nucleic acid delivery particles and optionally an excipient in a dry powder or lyophilized powder form. Prior to use, the physiologically acceptable diluent is added and the solution withdrawn via syringe for administration to an individual.

The nucleic acid delivery particles described herein may also be formulated for controlled release. As used herein, the term "controlled release" or "extended release" refers to release of an active agent (i.e., a nucleic acid) from a formulation or pharmaceutical composition at a rate such that the blood concentration of the agent in an individual is maintained within the therapeutic range for an extended duration, over a time period on the order of hours, days, weeks, or longer. The term also encompasses depot formulations designed to gradually release the drug compound over an extended period of time. Controlled release formulations can include a wide variety of drug delivery systems, generally involving mixing the drug compound with carriers, polymers or other compounds having the desired release characteristics (i.e., pH-dependent or non-pH-dependent solubility, different degrees of water solubility, and the like) and formulating the mixture according to the desired route of delivery (i.e., coated capsules, implantable reservoirs, injectable solutions containing biodegradable capsules, and the like). For example, nucleic acid delivery particles may be formulated in a bioerodible or nonbioerodible controlled matrix, a number of which are well known in the art. A controlled release matrix may include a synthetic polymer or copolymer, for example in the form of a hydrogel. Examples of such polymers include polyesters, polyorthoesters, polyanhydrides, polysaccharides, poly(phosphoesters), polyamides, polyurethanes, poly(imidocarbonates) and poly(phosphazenes), and poly-lactide-co-glycolide (PLGA), a copolymer of poly(lactic acid) and poly(glycolic acid). Collagen, albumin, and fibrinogen containing materials may also be used.

Nucleic acid delivery particles may be administered according to the methods described herein to treat a number of conditions characterized by aberrant gene expression, including, but not limited to, disease conditions or metabolic disorders. In some embodiments, delivery particles are co-administered with other conventional therapies, for example, as part of a multiple drug "cocktail," or in combination with one or more orally administered agents, for example, for treatment of a disease condition or metabolic disorder. Delivery particles may also be administered as insecticides or herbicides.

In one aspect, a method of delivering nucleic acid to a cell is provided, the method comprising contacting the cell with a nucleic acid delivery particle as described In any of the embodiments described herein. In another aspect, a method of detecting gene expression in a cell for diagnostic purposes is provided, the method comprising contacting the cell with a nucleic acid delivery particle as described In any of the embodiments described herein. In certain embodiments, the nucleic acid associated with the delivery particle binds or hybridizes to a target gene of interest and further includes a detectable moiety, such as a fluorophore, chromophore, radioisotope, enzyme, or other moiety. In certain embodiments, the method further comprises a step of detecting a signal emitted by the detectable moiety, and the level of gene expression corresponds to the intensity of the signal detected.

Targeted Delivery of Nucleic Acid Delivery Particles

A nucleic acid delivery particle of the invention may include a targeting functionality, for example to target the particles to a particular cell or tissue type, or to the infectious agent itself. In some embodiments, the particle includes a targeting moiety attached to a lipid-binding polypeptide or lipid component. In some embodiments, the nucleic acid that is associated with the particle has a targeting capability.

In some embodiments, by engineering receptor recognition properties into a lipid-binding polypeptide, such as an apolipoprotein molecule, the particles can be targeted to a specific cell surface receptor. For example, nucleic acid delivery particles may be targeted to a particular cell type known to harbor a particular type of infectious agent, for example by modifying the lipid-binding polypeptide component of the particles to render it capable of interacting with a receptor on the surface of the cell type being targeted. Alternatively, nucleic acid delivery particles may be targeted to particular cell types, for example, by modifying the lipid-binding polypeptide component of the particles to render it capable of interacting with an antigen on the surface of the cell type being targeted. Such modifications may include addition of a targeting moiety, such as an scFv that specifically binds the target antigen.

In one aspect, a receptor-mediated targeting strategy may be used to deliver antileishmanial agents to macrophages, which are the primary site of infection for protozoal parasites from the genus *Leishmania*. Examples of such species include *Leishmania major, Leishmania donovani*, and *Leishmania braziliensis*. Nucleic acid delivery particles containing an antileishmanial agent may be targeted to macrophages by altering the lipid-binding polypeptide component of the particles to confer recognition by the macrophage endocytic class A scavenger receptor (SR-A). For example, an apolipoprotein which has been chemically or genetically modified to interact with SR-A may be incorporated into nucleic acid delivery particles that contain one or more nucleic acids that are effective against *Leishmania* species, such as, for example, an siRNA targeting the *Leishmania* "mini-exon" sequence found at the 5' end of all *Leishmania* mRNA transcripts. Targeting of nucleic acid delivery particles that contain an antileishmanial agent specifically to macrophages may be used as a means of inhibiting the growth and proliferation of *Leishmania* spp.

In certain embodiments, targeting is achieved by modifying a lipid-binding polypeptide, such as an apolipoprotein, for incorporation into the nucleic acid delivery particle, thereby conferring SR-A binding ability to the particle. In certain embodiments, targeting is achieved by altering the charge density of the lipid-binding polypeptide by chemically modifying one or more lysine residues, for example with malondialdehyde, maleic anhydride, or acetic anhydride at alkaline pH (see, e.g., Goldstein et al. (1979) *Proc. Natl. Acad. Sci.* 98:241-260). In certain embodiments, Apo B-100 or a truncated form thereof, such as the N-terminal 17% of ApoB-100 (residues 1-782 of apoB-100), is modified by reaction with malondialdehyde. In certain embodiments, an apolipoprotein molecule, such as any of the apolipoproteins described herein, is chemically modified by, for example acetylation or maleylation, and incorporated into a nucleic acid delivery particle containing an anti-leishmanial nucleic acid.

In certain embodiments, SR-A binding ability is conferred upon a nucleic acid delivery particle by modifying the lipid-binding polypeptide by site-directed mutagenesis to replace one or more positively charged amino acids with a neutral or negatively charged amino acid.

Methods for Preparing Nucleic Acid Delivery Particles

Provided herein are processes for formulating nucleic acid delivery particles. In certain embodiments, the process comprises the steps of: contacting bilayer forming lipid vesicles with total lipid content of about 5% to about 100% of one or more cationic lipids with a nucleic acid to form a bilayer-forming lipid vesicle-nucleic acid mixture, and contacting the bilayer-forming lipid vesicle-nucleic acid mixture with a lipid-binding polypeptide. In certain embodiments, the one or more cationic lipids are selected from the group consisting of N-[1-(2,3-dioleyloxy)propyl]-N,N,N-trimethylammonium chloride (DOTMA), amidine, dimethyl-dioctadecyl ammonium bromide (DDAB), dimyristoyltrimethylammonium propane (DMTAP), and 1,2-dioleoyloxy-3-trimethylammoniopropane (DOTAP). In certain embodiments, the nucleic acid is a short interfering RNA (siRNA), a short hairpin RNA (shRNA), a micro RNA (miRNA), an antisense RNA, an antisense DNA, an aptamer, a ribozyme, or a plasmid. In certain embodiments, the nucleic acid is solubilized in dimethylsulfoxide (DMSO) prior to contacting the bilayer-forming lipid vesicles. It is intended that with respect to the methods of preparing the nucleic acid delivery particles described herein that the lipid vesicles may contain the various proportions/types of lipids as described herein with respect to the composition of the lipid bilayer.

In certain embodiments, the bilayer-forming lipid vesicle-nucleic acid mixture also includes a detergent, such as for example sodium cholate, cholic acid, or octyl glucoside, and the process further includes removing the detergent after the lipid-binding polypeptide has been added. Typically, the detergent is removed by dialysis or gel filtration. In one embodiment, the process includes combining bilayer-forming lipids and nucleic acid molecules in a solvent to form a bilayer-forming lipid vesicle-nucleic acid mixture, drying the mixture to remove the solvent (e.g., under a stream of $N_2$ and/or by lyophilization), contacting the dried mixture with a solution that includes a detergent to form a bilayer-forming lipid vesicle-nucleic acid-detergent mixture, adding lipid-binding polypeptide molecules to this mixture, and then removing the detergent. In certain embodiments, the bilayer-forming lipid vesicle-nucleic acid mixture does not include a detergent.

In certain embodiments, the nucleic acid delivery particles are prepared using a microfluidizer processor. This procedure employs high pressure, forcing the components together in a reaction chamber. In certain embodiments, the particles are prepared by incubation of a suspension of lipid vesicles containing a nucleic acid in the presence of a lipid-binding polypeptide, such as an apolipoprotein. In certain embodiments, the suspension is sonicated.

In certain embodiments, the nucleic acid delivery particles are prepared by a process comprising the steps of: forming an aqueous dispersion of lipid vesicles, wherein the lipid vesicles comprise bilayer-forming lipids and comprise between about 5% to about 100% of one or more cationic lipids, adding a nucleic acid to the lipid vesicle dispersion to form a lipid-vesicle-nucleic acid mixture, adding a lipid-binding polypeptide to the lipid vesicle-nucleic acid mixture to form a lipid-nucleic acid-lipid-binding polypeptide mixture, and incubating the lipid vesicle-nucleic acid-lipid-binding polypeptide mixture. In certain embodiments, the one or more cationic lipids are selected from the group consisting of N-[1-(2,3-dioleyloxy)propyl]-N,N,N-trimethylammonium chloride (DOTMA), amidine, dimethyl-dioctadecyl ammonium bromide (DDAB), dimyristoyltrimethylammonium propane (DMTAP), and 1,2-dioleoyloxy-3-trimethylammoniopropane (DOTAP). In certain embodiments, the nucleic acid is a short interfering RNA (siRNA), a short hairpin RNA (shRNA), a micro RNA (miRNA), an antisense RNA, an antisense DNA, an aptamer, a ribozyme, or a plasmid. In certain embodiments, the process further comprises sonicating the lipid vesicle-nucleic acid-lipid-binding polypeptide mixture after incubation. In certain embodiments, the nucleic acid is solubilized in DMSO before addition to the lipid vesicle dispersion. In certain embodiments, the nucleic acid is solubilized in another volatile or dialyzable solvent that can conveniently be removed after addition of solubilized nucleic acid to the lipid bilayer vesicle dispersion. Typically, the vesicles and apolipoprotein are incubated at or near the gel-to-liquid crystalline phase transition temperature of the particular bilayer-forming lipid or mixture of bilayer-forming lipids being used. The phase transition temperature may be determined by calorimetry.

In any of the embodiments described herein, the lipid bilayer comprises at least 25% and not more than 50% (i.e., between 25% and 49%, between 25% and 45%, between 25% and 40%, between 25% and 35%, or between 25% and 30%) of one or more cationic lipids and between at least 50% and not more than 75% of one or more phospholipids. In any of the embodiments described herein, the lipid bilayer comprises at least 30% and not more than 50% (i.e., between 30% and 49%, between 30% and 45%, between 30% and 40%, or between 30% and 35%) of one or more cationic lipids and between at least 50% and not more than 70% of one or more phospholipids. In any of the embodiments described herein, the lipid bilayer comprises at least 35% and not more than 50% (i.e., between 35% and 49%, between 35% and 45%, or between 35% and 40%) of one or more cationic lipids and between at least 50% and not more than 65% of one or more phospholipids. In certain embodiments, the one or more cationic lipids is dimyristoyltrimethylammonium propane (DMTAP).

In any of the embodiments described herein, the total lipid content of the lipid vesicles includes about 30% of one or more cationic lipids and about 70% of one or more phospholipids. In some embodiments, the one or more phospholipids is dimyristoylphosphatidylcholine (DMPC). In some embodiments, the one or more cationic lipids is dimyristoyltrimethylammonium propane (DMTAP). In any of the embodiments described herein, the total lipid content of the lipid vesicles includes about 30% of one or more cationic lipids and about 70% of dimyristoylphosphatidylcholine (DMPC). In any of the embodiments described herein, the total lipid content of the lipid vesicles includes about 30% of dimyristoyltrimethylammonium propane (DMTAP) and about 70% of one or more phospholipids. In any of the embodiments described herein, the total lipid content of the lipid vesicles includes about 30% of dimyristoyltrimethylammonium propane (DMTAP) and about 70% of dimyristoylphosphatidylcholine (DMPC).

In certain embodiments, a suitable bilayer-forming lipid composition is used such that, upon dispersion in aqueous media, the lipid vesicles provide a suitable environment to transition a nucleic acid from a carrier solvent into an aqueous milieu without precipitation or phase separation of the nucleic acid. The pre-formed lipid bilayer vesicles are also preferably capable of undergoing lipid-binding polypeptide-induced transformation to form the nucleic acid delivery particles of the invention. Further, the lipid-nucleic acid complex preferably retains properties of the lipid vesicles that permit transformation into nucleic acid delivery particles upon incubation with a lipid-binding polypeptide under appropriate conditions. The unique combination of lipid substrate-nucleic acid complex organization and lipid-binding polypeptide properties combine to create a system whereby, under appropriate conditions of pH, ionic strength, temperature, and lipid, nucleic acid, and lipid-binding polypeptide concentration, a ternary structural reorganization of those materials occurs wherein stable lipid bilayers are created with lipid-binding polypeptide circumscribing the bilayer and a nucleic acid associated with the surface of the bilayer. For a discussion of the effect of pH, ionic strength and lipid-binding polypeptide concentration on the ability of lipid-binding polypeptides to induce transformation of different types of phospholipid vesicles into disc shaped particles, see Weers et al. (2001) *Eur. J. Biochem.* 268:3728-35.

In any of the embodiments described herein, the nucleic acid delivery particles may be further purified, for example by dialysis, density gradient centrifugation and/or gel permeation chromatography. In any of the embodiments described herein, the nucleic acid may be added to the nucleic acid delivery particles after formation of the lipid bilayers.

Preparation of Nanodisks Incorporating Hydrophobic Bioactive Agents has been reported using a combination of anionic and zwitterionic bilayer forming phospholipids (Oda, M. N., Hargreaves, P, Beckstead, J. A., Redmond, K. A., van Antwerpen, R. and Ryan, R. O. (2006) Reconstituted high-density lipoprotein enriched with the polyene antibiotic, amphotericin B. *J. Lipid Res.* 47, 260-267). Because the nucleic acids can be added to pre-formed lipid bilayer/lipid binding polypeptide particles after generation of the complexes, an alternative method for nucleic acid delivery particle production, namely the cholate dialysis method (Jonas A. (1986) Reconstitution of high-density lipoproteins. *Methods Enzymol.* 128, 553-582 (incorporated herein by reference in its entirety), may also be employed. In this method the lipid components are solubilized in detergent (cholate or deoxycholate) followed by addition of lipid binding polypeptide and exhaustive dialysis to remove the detergent. This method yields disk particles from lipids that are unable to form nanodisks by the direct solubilization method and hence, may be useful for the preparation of the nucleic acid delivery particles as described herein. In certain embodiments, the lipid bilayer-lipid-binding polypeptide particles are made as described above but in the absence of nucleic acid and subsequently incubated with nucleic acid.

Also provided herein are nucleic acid delivery particles prepared by any of the above methods. In one embodiment, the invention provides a pharmaceutical composition comprising a nucleic acid delivery particle prepared by any of the above methods and a pharmaceutically acceptable carrier.

Storage and Stability

The nucleic acid delivery particles provided herein are stable for long periods of time under a variety of conditions. Stable particles remain disc-shaped, retain the positive charge conferred by incorporation of cationic lipids, and retain the nucleic acids associated with the particle in aqueous solution. In certain embodiments, nucleic acid delivery particles, or compositions comprising nucleic acid delivery particles, are stored at room temperature, refrigerated (e.g., at about 4° C.), or frozen (e.g., at about −20° C. to about −80° C.). In certain embodiments, the nucleic acid delivery particles, or compositions comprising nucleic acid delivery particles are stored in solution or dried (e.g., lyophilized). In certain embodiments, the nucleic acid delivery particles, or compositions comprising nucleic acid delivery particles are stored in a lyophilized state under inert atmosphere, frozen, or in solution at 4° C. In certain embodiments, the nucleic acid delivery particles, or compositions comprising nucleic acid delivery particles are stored in a liquid medium, such as a buffer (e.g., phosphate or other suitable buffer), or in a carrier, such as for example a pharmaceutically acceptable carrier, for use in methods of administration of a nucleic acid to an individual. In certain embodiments, the nucleic acid delivery particles, or compositions comprising nucleic acid delivery particles are stored in a dried, lyophilized form and then reconstituted in liquid medium prior to use.

Kits

The reagents and nucleic acid delivery particles described herein can be packaged in kit form. In one aspect, kits are provided that include delivery particles and/or reagents useful for preparing nucleic acid delivery particles, in suitable packaging. In certain embodiments, the kits any of the following, separately or in combination: lipid-binding polypeptides (e.g., apolipoproteins), phospholipids, cationic lipids, nucleic acids (i.e., a short interfering RNA (siRNA), a short hairpin RNA (shRNA), a micro RNA, an antisense RNA, an antisense DNA, an aptamer, a ribozyme, or a plasmid), vectors, reagents, enzymes, host cells and/or growth medium for cloning and/or expression of recombinant lipid-binding polypeptides (e.g., recombinant apolipoproteins) and/or lipid-binding polypeptide chimeras (e.g., apolipoprotein chimeras), and reagents and/or pharmaceutically acceptable carriers for formulating nucleic acid delivery particles for administration to an individual, or to a cell.

Each reagent or formulation is supplied in a solid form, liquid buffer, or pharmaceutically acceptable carrier that is suitable for inventory storage, or optionally for exchange or addition into a reaction, culture, or injectable medium. Suitable packaging is provided. As used herein, the term "packaging" refers to a solid matrix or material customarily used in a system and capable of holding within fixed limits one or more of the reagents or components (e.g., nucleic acid delivery particles) for use in a method for delivery of a nucleic acid (i.e., a short interfering RNA (siRNA), a short hairpin RNA (shRNA), a micro RNA, an antisense RNA, an antisense DNA, an aptamer, a ribozyme, or a plasmid) or one or more reagents for preparing or formulating nucleic acid delivery particles (e.g., apolipoprotein molecules, phospholipids, bioactive agents). Such materials include, but are not limited to, glass and plastic (e.g., polyethylene, polypropylene, and polycarbonate) bottles, vials, paper, plastic, and plastic-foil laminated envelopes, and the like.

A kit may optionally provide additional components useful in the practicing the methods and preparing the formulations described herein, such as buffers, reacting surfaces, or means of preparing and/or purifying nucleic acid delivery particles. In addition, the kits optionally include labeling and/or instructional or interpretive materials providing directions (i.e., protocols) for the practice of any of the methods described herein, such as preparation, formulation and/or use of nucleic acid delivery particles. While the instructional materials typically comprise written or printed materials they are not limited to these formats. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to Internet sites that provide such instructional materials.

The following examples are intended to illustrate but not limit the invention.

EXAMPLES

Example 1

Preparation and Characterization of Lipophilic Nucleic Acid Delivery Particles

Preparation of Recombinant ApoA-I

Recombinant Apo-A-I was prepared as described in Ryan et al. (2003) *Prot. Expr. Purif.* 27:98-103, and was used to prepare Apo-A-1-cationic lipid particles as described below.
Preparation of Cationic Lipid Nanodisks Initial experiments used the commercially available cationic lipid dimyristoyltrimethylammonium propane (DMTAP; see FIG. 1). The amount of DMTAP was systematically increased from 0 to 50% in 10% increments, and the amount of dimyristoylphosphatidylcholine (DMPC) used systematically decreased in 10% increments. Lipid bilayers prepared with varying ratios of DMTAP to DMPC were made with apolipoprotein ("apo") A-I. Other scaffold proteins and peptides will be incorporated in the future. The data showed that apolipoprotein ("apo") A-I efficiently induced formation of nanodisk particles at DMTAP amounts up to 30% (w/w) versus DMPC amounts increasing from 70% (w/w). At higher concentrations of DMTAP, the resulting nanodisks were less stable and tended to precipitate from solution over time.

Figure 3:
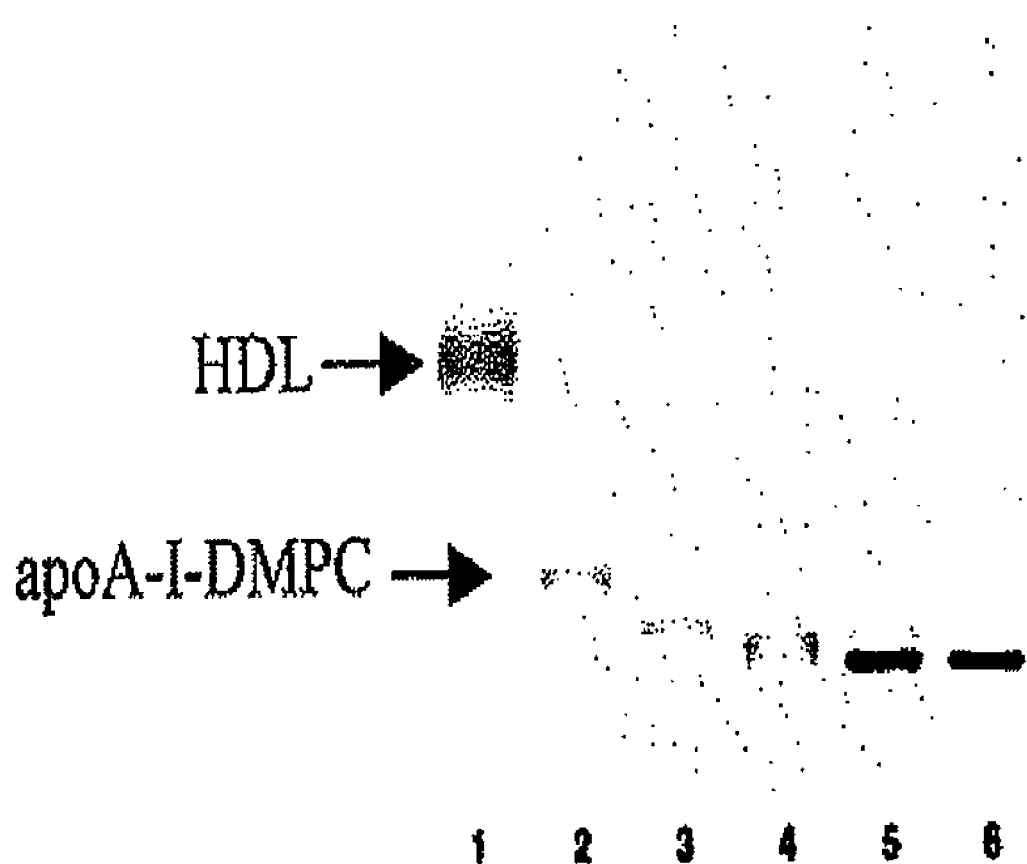
FIG. 3 shows an agarose gel separating nanodisk particles incorporating cationic lipids. Samples were electrophoresed on a "Lipo-Gel" agarose gel per the manufacturer's instructions. Lane 1) control HDL, Lane 2) DMPC nanodisk ("ND"), Lane 3) 5% DMTAP ND, Lane 4) 10% DMTAP ND, Lane 5) 15% DMTAP ND and Lane 6) 20% DMTAP ND. All ND preparations used apoA-I as the scaffold protein.

Based on those results, nanodisks comprising 30% (w/w) DMTAP, 70% (w/w) DMPC and apoA-I were used for initial characterization studies. Following preparation of the 30% DMTAP/70% DMPC/apoA-I nanodisks, the particles were incubated with siRNA targeting GAPDH as described in Example 2. Empty nanodisks were diluted to a volume of 25 µl or 50 µl with serum free OPTI-MEM growth medium (GIBCO™, Invitrogen, Carlsbad, Calif.) and incubated for 10 minutes at room temperature. After that incubation, GAPDH siRNA or negative control siRNA was diluted to a volume of 25 µl or 50 µl in serum-free OPTI-MEM growth medium, producing an siRNA concentration between 3 nM and 50 nM, and added to the empty nanodisks for a total reaction volume of 50 µl or 100 µl. The nanodisk/siRNA mixtures were then incubated for ten minutes at room temperature and used in transfection experiments as described in Example 2 below.
Characterization and Visualization of Cationic Lipid Nanodisks Native pore limiting polyacrylamide gel electrophoresis of nanodisks comprising 30% (w/w) DMTAP, 70% (w/w) DMPC and apoA-I failed to give rise to a distinct band, possibly because of the increased positive charge contributed by the DMTAP. To investigate this further we employed "Lipo-Gel" agarose gels in lieu of polyacrylamide, according to the manufacturer's instructions. In this case, cationic lipid nanodisks migrated as a distinct band that, compared to control high-density lipoprotein (HDL) and 100% (w/w) DMPC nanodisks, did not migrate as far into the gel (FIG. 3). These data are consistent with incorporation of cationic lipid into the nanodisk particle structure.

Figure 4:
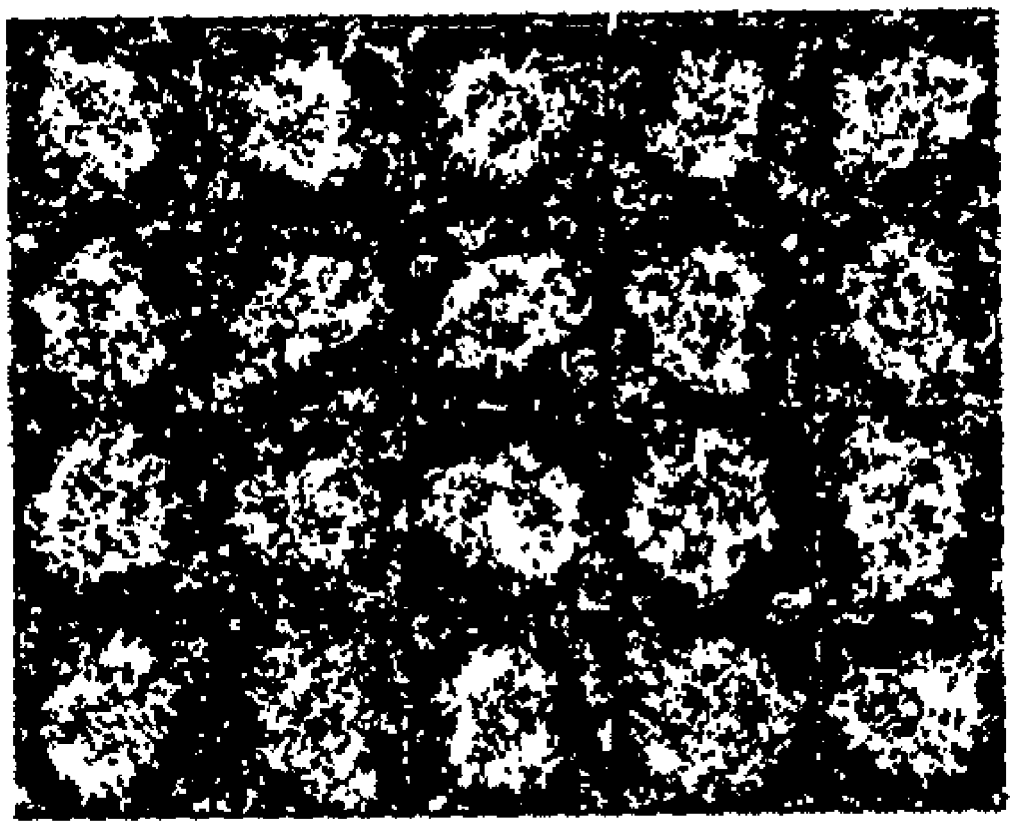
FIG. 4 is an electron micrograph showing morphology of nanodisks containing 30% DMTAP (i.e., nucleic acid delivery particles) by negative stain electron microscopy. Each box=30 nm.

Negative stain electron microscopy of cationic lipid nanodisks revealed a morphology that is consistent with a disk-shaped structure in which the lipid component exists as a bilayer (FIG. 4). This interpretation has been largely confirmed by atomic force microscopy experiments that also show a disk-shaped morphology. Of particular interest is the finding that, when cationic lipid nanodisks were incubated with siRNA, atomic force microscopy analysis revealed an increase in particle width that is consistent with interaction of the disk complex and the nucleic acid (not shown). This observation revealed that cationic lipid ND structure/morphology was not compromised by interaction with siRNA.
Optimization of Cationic Lipid Nanodisk Structure and Stability Prior to conducting studies with siRNA, a set of cationic lipid nanodisk particles is produced and characterized in terms of particle stability. Initially the extent to which different cationic lipids can be incorporated into nanodisks and the percentage at which they can be introduced with retention of nanodisk particle integrity is determined. Those studies are performed with recombinant apoA-I as the scaffold protein (Ryan, R. O., Forte T. M. and Oda, M. N. (2003) Optimized bacterial expression of human apolipoprotein A-I. *Protein Expr. Purif.* 27, 98-103). This 243 amino acid protein can be produced in large quantities and is well known to induce nanodisk particle formation under appropriate experimental conditions.

Control nanodisks containing phosphatidylcholine (PC) as the sole lipid are formed and reaction progress monitored by right angle light scattering (Hargreaves, P. L., Nguyen, T-S, and Ryan, R. O. (2006) Spectroscopic studies of amphotericin B solubilized in nanoscale bilayer membranes. *Biochim. Biophys. Acta* 1758, 38-44). The cationic lipids to be employed are DOTMA (Feigner, P. L., Gadek, T. R., Holm, M., Roman, R., Chan, H. W., Wenz, M., Northrop, J. P., Ringold, G. M., and Danielsen, M. (1987) Lipofection: a highly efficient, lipid-mediated DNA-transfection procedure.

*Proc. Natl. Acad. Sci. U.S.A.* 84, 7413-7417), amidine (Ruysschaert, J. M., El Ouahabi, A., Willeaume, V., Huez, G., Fuks, R., Vandenbranden, M. and Di Stefano, P. (1994) A novel cationic amphiphile for transfection of mammalian cells. *Biochem. Biophys. Res. Commun.* 203, 1622-1628), DDBA (Zhu, N., Liggitt, D., Liu, Y. and Debs, R. (1993) Systemic Gene Expression after Intravenous DNA Delivery into Adult Mice. *Science.* 261, 209-211), DMTAP (see above) and DOTAP (Stamatatos, L., Leventis, R., Zuckermann, M. J., Silvius, J. R. (1988) Interactions of cationic lipid vesicles with negatively charged phospholipid vesicles and biological membranes. *Biochemistry.* 27, 3917-3925). These lipids are initially incubated with DMPC at 10%, 20%, 30%, and 40% by weight versus DMPC, producing nanodisks with 10% cationic lipid/90% DMPC, 20% cationic lipid/80% DMPC, 30% cationic lipid/70% DMPC, and 40% cationic lipid and 60% DMPC. The amount of cationic lipid may also be increased, and other cationic lipids may be tested.

Determining the siRNA Binding Capacity of Cationic Lipid Nanodisks

The hypothesis that siRNA binds to nanodisks as a function of increasing positive charge character conferred by cationic lipid is tested. Nanodisks are attractive candidate vehicles for delivering nucleic acid therapeutics such as siRNA because the particles are of nanometer scale size (10-20 nm diameter), the fact that both surfaces of the disk are available for siRNA binding, and the presence of an integrally associated protein that can serve as a ligand for endocytic cell surface receptors, enabling targeted delivery of nucleic acids. The interaction of siRNA with cationic lipid ND is evaluated by gel filtration chromatography of the complexes. siRNA obtained from a commercial vendor is used in binding experiments. A fluorescence-tagged siRNA is added to the mixture to facilitate monitoring of the binding interaction. The optimized cationic lipid nanodisk preparation obtained by the experiments described in Example 1 is incubated with siRNA and the mixture subjected to gel permeation chromatography.

Stable binding interaction between cationic lipid nanodisks and siRNA is confirmed by elution of the siRNA/nanodisk complex from the gel filtration column as a single peak. The column effluent is monitored for unbound siRNA (detected by fluorescence), protein and lipid using standard assay methods. Control experiments are performed using cationic lipid nanodisks without siRNA, with siRNA alone, as well as with DMPC lipid nanodisks with siRNA. In the latter case, it is expected that no interaction will occur and the siRNA and nanodisk components are observed to elute separately from the column.

Nanodisk aggregation may occur upon complex formation with siRNA because of charge attraction between nanodisk particles. If stable aggregates form, this will likely affect the gel filtration elution profile. The potential for aggregation is investigated by electron microscopy. If evidence of aggregation is obtained, the ratio of siRNA to cationic lipid is adjusted to minimize the effect.

Example 2

Knockdown of GAPDH Expression by Nucleic Acid Delivery Particles Comprising an siRNA siRNA-loaded cationic lipid nanodisks are compared to conventional cationic lipid transfection reagents in gene knockdown experiments. Targeting of siRNA to cell surface endocytic receptors is investigated using nanodisk particles generated with apoE or apoA-I as the scaffold protein.

For siRNA gene knockdown experiments, the KDalert™ GAPDH Assay Kit (Ambion, Inc., Austin, Tex.) is used according to the manufacturer's instructions, modified as discussed below. The KDalert™ GAPDH Assay Kit is designed as an assessment tool for siRNA transfection optimization, and is used to measure gene silencing or knockdown of GAPDH (glyceraldehyde 3-phosphate dehydrogenase) at the protein level. In this assay, Hep3B or HEK 293 cells are transfected with GAPDH siRNA or negative control siRNA. Efficacy of cationic lipid nanodisks as transfection reagent is assessed using GAPDH-specific siRNA and negative control siRNA. Cells are also incubated with control transfection agents that are commercially available, such as Lipofectamine™ (Invitrogen, Carlsbad, Calif.) or siPORT NeoFX™ (Ambion, Inc., Austin, Tex.). Forty-eight hours after transfection, the difference in gene knockdown by cationic lipid nanodisks and commercially available siRNA transfection reagents is assessed.

The ability of siRNA-loaded cationic lipid nanodisks to target delivery of siRNA to cells via receptor mediated endocytosis is also assayed. ApoE is a known ligand for the low-density lipoprotein (LDL) receptor, while ApoA-I does not bind the LDL receptor. Therefore, cationic lipid nanodisks are made by the processes disclosed herein using apoE or apoA-I as the nanodisk scaffold protein, each loaded with GAPDH siRNA. GAPDH siRNA enriched cationic lipid nanodisks made with apoE or made with apoA-I are assayed for the ability to downregulate GAPDH expression in cultured cells. It is expected that LDL receptor-mediated uptake of siRNA delivered via apoE-containing nanodisks will enhance efficiency of GAPDH downregulation compared to apoA-1-containing nanodisks.

Example 3

Long Term Stability of Nucleic Acid Delivery Particles

Recombinant ApoE3NT-terminal domain (ApoE3NT) is prepared as in Fisher et al. (1997) *Biochem Cell Biol* 75:45-53. ApoE3NT-containing particles are prepared via the cholate dialysis method described above, and used to assess long-term stability of the cationic lipid-containing nanodisks without nucleic acid.

Stability of nanodisk particles is assessed by native PAGE 4-20% gradient slab gel of particles stored in phosphate buffer at 4° C., stored in phosphate buffer at −20° C., or frozen in phosphate buffer at −80° C., lyophilized, and redissolved in $H_2O$ prior to analysis. The size and mobility of the cationic lipid-containing particles were unaffected by freezing and thawing, or by lyophilization and resolubilization, indicating that the particles retained their integrity under these conditions. These are important parameters with regard to scale up and long-term storage of nucleic acid delivery particles.

Those experiments are repeated with cationic lipid-containing nanodisks loaded with various different nucleic acids. In addition to evaluating long-term stability of the cationic lipid-containing nanodisks, the nanodisks are loaded with different nucleic acids are subjected to various storage conditions and then assayed for their ability to down regulate gene expression as discussed in Example 2 above.

Example 4

Silencing of ApoB-100 with siRNA Delivered by Cationic Lipid Nanodisks

To silence the apolipoprotein B (ApoB) gene in vivo, cationic lipid nanodisks (CL ND) have to stably bind short interfering RNA targeting the ApoB gene (siApoB) (see, e.g., NCBI Reference Sequence: NG_011793.1 (*Homo sapiens* apolipoproteinB gene) and NCBI Reference Sequence: NM_009693.2 (*Mus musculus* Apolipoprotein B mRNA)) and transport it from the site of injection to the targeted tissue in the liver. An siRNA sequence can be selected to silence both ApoB-48 and ApoB-100, depending on the siRNA employed. ApoB-48 is produced from the same mRNA transcript as ApoB-100, after RNA editing to introduce a stop codon at residue 2153. An siRNA targeting a sequence upstream of that residue would silence both ApoB-48 and ApoB-100, while an siRNA targeting a sequence downstream of that residue would silence only ApoB-100. These experiments are done in parallel with an siRNA that silences both ApoB-48 and ApoB-100 and with an siRNA that silences only ApoB-100.

To determine plasma stability and time-dependent tissue distribution of CL ND loaded with siRNA, $^{32}$P-labeled control siRNA (siCNT) is used. A single dose of $^{32}$P-labeled siCNT is delivered into mice via tail vein injection either as naked RNA or loaded onto CL ND (CL-siCNT-ND), and mice are sacrificed 1, 4 and 24 hours after administration. Blood, kidney, liver, jejunum, lung and brain are harvested. Total RNA is isolated from tissue homogenates and subjected to agarose gel electrophoresis, Northern blotting and autoradiography to detect intact siRNA.

Time-dependent tissue distribution of CL-siCNT-ND is assessed by monitoring levels of radioactivity in a variety of tissue samples. Significant accumulation of intact siRNA is expected to occur in liver over time for a CL ND formulation that stably binds siRNA. Distribution to non-specific tissue such as jejunum and lung is assessed to determine feasibility of selective organ delivery with CL ND. Radioactivity detected in blood and kidney over time is measured to shed light on rate of clearance. Naked siCNT is expected to accumulate in the kidneys shortly after administration, in part because the sub-nanometric dimension of siRNA and its anionic charge is expected to result in rapid plasma clearance of siRNA delivered without a carrier.

ApoB knockdown efficiency and concomitant toxicity of CL ND is determined in two groups of mice, one group fed normal animal chow (chow-fed) and one fed a high fat diet. Therapeutically effective doses in the two groups are expected to be different. This will reveal the safety of CL ND formulated with siRNA across a broad dosage spectrum.

Each group of mice is divided into four treatment arms: (1) saline only; (2) CL-siApoB-ND; (3) CL-siCNT-ND; and (4) empty CL ND. Dose-dependent effect of each treatment on serum ApoB protein levels is followed over time after a single injection. Measurement of knockdown in ApoB protein level as a function of time will reveal both the time from injection to onset of silencing and the duration of silencing, taking into account the lag period between knockdown at the level of mRNA transcription and observation of a reduction at the level of serum protein concentrations.

Hepatic ApoB mRNA levels are quantitated and normalized relative to mRNA levels of the housekeeping gene glyceraldehyde-3-phosphate dehydrogenase (Gapdh). With protein and mRNA levels for the control group treated with saline set at 100 percent, the percent remaining expression for the CL-siApoB-ND, CL-siCNT-ND and empty CL ND treatment arms is computed and compared. Animals receiving CL-siApoB-ND display dose-dependent silencing of ApoB relative to the control group treated with saline. No silencing is observed in animals receiving CL-siCNT-ND or empty CL ND.

ApoB mRNA levels in the jejunum are also quantitated and normalized as described for the hepatic samples. The tissue biodistribution data corresponds with ApoB mRNA knockdown effects observed in the CL-siApoB-ND treatment arm.

ELISA-based screens are used to quantitate serum alanine aminotransferase, aspartate aminotransferase, IFN-α, IFN-γ, TNF-α and IL6 levels in animals from all four treatment arms in both chow-fed and high fat diet groups at multiple time points. To fully investigate any perturbation of gene expression level, tissues that selectively take up siRNA (as determined from the biodistribution data) is harvested from animals in the CL-siCNT-ND and saline treatment arms. Total RNA is isolated from each tissue. Then cDNA is synthesized, labeled, fragmented, and hybridized to a mouse genome chip using methods outlined by manufacturer (Affymetrix, Santa Clara, Calif.). Animals from the CL-siCNT-ND treatment arm are selected since changes in the gene expression profile for this group relative to the saline control group are expected to identify CL ND-specific effects.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention, which is delineated by the appended claims.

All publications, patents, and patent applications cited herein are hereby incorporated by reference in their entirety for all purposes and to the same extent as if each individual publication, patent, or patent application were specifically and individually indicated to be so incorporated by reference.

I claim:

1. A nucleic acid delivery particle comprising a lipid-binding polypeptide, a lipid bilayer, and a nucleic acid,
   wherein the total lipid content of the lipid bilayer is between about 5% and about 100% of one or more cationic lipids,
   wherein the interior of the lipid bilayer comprises a hydrophobic region,
   wherein the particle
   does not comprise an aqueous core,
   is disc-shaped with the hydrophobic edge of the lipid bilayer circumscribed by the lipid-binding polypeptide at the periphery of the particle, and
   remains disc-shaped in aqueous solution.

2. A nucleic acid delivery particle according to claim 1, wherein the particle does not comprise a hydrophilic core.

3. A nucleic acid delivery particle according to claim 1, wherein the disc shaped particle is between about 10 nm to about 40 nm in diameter.

4. A nucleic acid delivery particle according to claim 1, wherein the one or more cationic lipids is selected from the group consisting of N-[1-(2,3-dioleyloxy)propyl]-N,N,N-trimethylammonium chloride (DOTMA), amidine, dimethyldioctadecyl ammonium bromide (DDAB), dimyristoyltrimethylammonium propane (DMTAP), and 1,2-dioleoyloxy-3-trimethylammoniopropane (DOTAP).

5. A nucleic acid delivery particle according to claim 1, wherein the total lipid content of the lipid bilayer is between about 0% to about 95% of one or more phospholipids.

6. A nucleic acid delivery particle according to claim 5, wherein the one or more phospholipids is selected from the group consisting of dimyristoylphosphatidylcholine (DMPC) and dimyristoylphosphatidylglycerol (DMPG).

7. A nucleic acid delivery particle according to claim 5, wherein the one or more phospholipids is selected from the group consisting of dipalmitoylphosphatidylcholine (DPPC) and egg phosphatidylcholine.

8. A nucleic acid delivery particle according to claim 1, wherein the nucleic acid is a short interfering RNA (siRNA), a short hairpin RNA (shRNA), a micro RNA, an antisense RNA, an antisense DNA, an aptamer, a ribozyme, or a plasmid.

9. A nucleic acid delivery particle according to claim 8, wherein the nucleic acid associates with the surface of the particle by electrostatic interactions.

10. A nucleic acid delivery particle according to claim 8, wherein the nucleic acid further comprises a lipophilic conjugate, and wherein the lipophilic conjugate is incorporated into the hydrophobic region of the lipid bilayer.

11. A nucleic acid delivery particle according to claim 10, wherein the lipophilic conjugate is selected from the group consisting of cholesterol, oleic acid, stearic acid, palmitic acid, myristic acid, and linoleic acid.

12. A nucleic acid delivery particle according to claim 1, wherein the lipid-binding polypeptide is an apolipoprotein.

13. A nucleic acid delivery particle according to claim 12, wherein the apolipoprotein is an exchangeable apolipoprotein.

14. A nucleic acid delivery particle according to claim 13, wherein the apolipoprotein is human apolipoprotein A-I.

15. A nucleic acid delivery particle according to claim 12, wherein the apolipoprotein is a chimeric apolipoprotein that comprises a functional moiety.

16. A nucleic acid delivery particle according to claim 15, wherein the functional moiety is a targeting moiety.

17. A nucleic acid delivery particle according to claim 12, wherein the apolipoprotein has been modified to increase stability of the particle.

18. A nucleic acid delivery particle according to claim 17, wherein the modification comprises introduction of cysteine residues to form intermolecular or intramolecular disulfide bonds.

19. A nucleic acid delivery particle according to claim 18, wherein the apolipoprotein is modified to present uncharged amino acids in regions of the apolipoprotein adjacent to the head groups of the one or more cationic lipids.

20. A nucleic acid delivery particle according to claim 12, wherein the lipid-binding polypeptide is a peptide.

21. A nucleic acid delivery particle according to claim 20, wherein the lipid-binding polypeptide is an amphipathic peptide.

22. A nucleic acid delivery particle according to claim 20, wherein the peptide has been modified to increase stability of the particle.

23. A nucleic acid delivery particle according to claim 22, wherein the peptide is modified to present uncharged amino acids in regions of the peptide adjacent to the head groups of the one or more cationic lipids.

24. A pharmaceutical composition for the delivery of a nucleic acid comprising a nucleic acid delivery particle according to claim 1 and a pharmaceutically acceptable carrier.

25. A pharmaceutical composition according to claim 24, wherein the composition is formulated for controlled release.

26. A method for in vivo administration of a nucleic acid, comprising administering an effective amount of the pharmaceutical composition of claim 24 to an individual.

27. A method according to claim 26, wherein the pharmaceutical composition comprises a therapeutically effective amount of the nucleic acid.

28. A method according to claim 27, wherein the nucleic acid is a short interfering RNA (siRNA), a short hairpin RNA (shRNA), a micro RNA, an antisense RNA, an antisense DNA, an aptamer, a ribozyme, or a plasmid.

29. A method according to claim 26, wherein the administration is parenteral.

30. A method according to claim 29, wherein the parenteral administration is selected from the group consisting of intravenous, intramuscular, transmucosal, and intrathecal.

31. A method according to claim 26, wherein the composition is administered as an aerosol.

32. A method according to claim 26, wherein the composition is formulated for controlled release.

33. A process for formulating a nucleic acid delivery particle according to claim 1, the process comprising:
    (1) contacting bilayer-forming lipid vesicles with a nucleic acid to form a bilayer-forming lipid vesicle-nucleic acid mixture, wherein about 5% to about 100% of the total lipid content of the vesicles is one or more cationic lipids, and
    (2) contacting the bilayer-forming lipid vesicle-nucleic acid mixture with a lipid-binding polypeptide.

34. A process according to claim 33, wherein the one or more cationic lipids is selected from the group consisting of N-[1-(2,3-dioleyloxy)propyl]-N,N,N-trimethylammonium chloride (DOTMA), amidine, dimethyl-dioctadecyl ammonium bromide (DDAB), dimyristoyltrimethylammonium propane (DMTAP), and 1,2-dioleoyloxy-3-trimethylammoniopropane (DOTAP).

35. A process according to claim 33, wherein the nucleic acid is a short interfering RNA (siRNA), a short hairpin RNA (shRNA), a micro RNA, an antisense RNA, an antisense DNA, an aptamer, a ribozyme, or a plasmid.

36. A process according to claim 35, wherein the nucleic acid is solubilized in dimethylsulfoxide (DMSO) prior to contacting the bilayer-forming lipid vesicles.

37. A process for formulating a nucleic acid delivery particle according to claim 1, said process comprising the steps of:
    (1) forming an aqueous dispersion of lipid vesicles, wherein said lipid vesicles comprise bilayer-forming lipids and about 5% to about 100% of total lipid content of the vesicles is one or more cationic lipids;
    (2) adding a nucleic acid to the lipid vesicle dispersion to form a lipid vesicle-nucleic acid mixture;
    (3) adding a lipid-binding polypeptide to the lipid vesicle-nucleic acid mixture to form a lipid-nucleic acid-lipid-binding polypeptide mixture; and
    (4) incubating the mixture formed in step (3).

38. A process according to claim 37, wherein the one or more cationic lipids is selected from the group consisting of N-[1-(2,3-dioleyloxy)propyl]-N,N,N-trimethylammonium chloride (DOTMA), amidine, dimethyl-dioctadecyl ammonium bromide (DDAB), dimyristoyltrimethylammonium propane (DMTAP), and 1,2-dioleoyloxy-3-trimethylammoniopropane (DOTAP).

39. A process according to claim 37, wherein the nucleic acid is a short interfering RNA (siRNA), a short hairpin RNA (shRNA), a micro RNA, an antisense RNA, an antisense DNA, an aptamer, a ribozyme, or a plasmid.

40. A process for formulating a nucleic acid delivery particle according to claim 37, wherein the process further comprises sonicating the mixture of step (4).

41. A process according to claim 39, wherein the nucleic acid is solubilized in DMSO prior to addition to the lipid vesicle dispersion.

42. A nucleic acid delivery particle prepared according to the process of claim 33.

43. A nucleic acid delivery particle according to claim 42, wherein the nucleic acid is a short interfering RNA (siRNA), a short hairpin RNA (shRNA), a micro RNA, an antisense RNA, an antisense DNA, an aptamer, a ribozyme, or a plasmid.

44. A nucleic acid delivery particle prepared according to the process of claim 37.

45. A nucleic acid delivery particle according to claim 44, wherein the nucleic acid is a short interfering RNA (siRNA), a short hairpin RNA (shRNA), a micro RNA, an antisense RNA, an antisense DNA, an aptamer, a ribozyme, or a plasmid.

46. A pharmaceutical composition comprising a nucleic acid delivery particle according to claim 42 and a pharmaceutically acceptable carrier.

47. A pharmaceutical composition according to claim 46, wherein the nucleic acid is a short interfering RNA (siRNA), a short hairpin RNA (shRNA), a micro RNA, an antisense RNA, an antisense DNA, an aptamer, a ribozyme, or a plasmid.

48. A pharmaceutical composition comprising a nucleic acid delivery particle according to claim 44 and a pharmaceutically acceptable carrier.

49. A pharmaceutical composition according to claim 48, wherein the nucleic acid is a short interfering RNA (siRNA), a short hairpin RNA (shRNA), a micro RNA, an antisense RNA, an antisense DNA, an aptamer, a ribozyme, or a plasmid.

50. A kit comprising a pharmaceutical composition according to claim 24 and instructions for use in a method for administering a nucleic acid to an individual.

51. A kit comprising a pharmaceutical composition according to claim 46 and instructions for use in a method for administering a nucleic acid to an individual.

52. A kit comprising a pharmaceutical composition according to claim 48 and instructions for use in a method for administering a nucleic acid to an individual.

53. A composition for delivery of a nucleic acid to an individual, comprising a nucleic acid delivery particle of claim 1 and a carrier.

54. A composition according to claim 53, wherein the individual is a plant or an insect.

55. A composition according to claim 53, wherein the nucleic acid is a short interfering RNA (siRNA), a short hairpin RNA (shRNA), a micro RNA, an antisense RNA, an antisense DNA, an aptamer, a ribozyme, or a plasmid.

56. A method for delivering a nucleic acid to a cell comprising contacting the cell with a nucleic acid delivery particle according to claim 1.

\* \* \* \* \*

UNITED STATES PATENT AND TRADEMARK OFFICE
CERTIFICATE OF CORRECTION

| | | |
|---|---|---|
| PATENT NO. | : 8,268,796 B2 | Page 1 of 1 |
| APPLICATION NO. | : 12/997976 | |
| DATED | : September 18, 2012 | |
| INVENTOR(S) | : Robert O. Ryan | |

It is certified that error appears in the above-identified patent and that said Letters Patent is hereby corrected as shown below:

In the Specification:

In Column 1, lines 17-19, please replace:

"This invention was made with government support under grant no. HL-64159 awarded by the National Institutes of Health. The government has certain rights in the invention."

with:

--This invention was made with government support under federal grant no. HL064159 from the National Institutes of Health. The government has certain rights in this invention.--

Signed and Sealed this
Thirteenth Day of May, 2014

Michelle K. Lee
*Deputy Director of the United States Patent and Trademark Office*